United States Patent [19]
Firestein et al.

[11] Patent Number: 6,004,942
[45] Date of Patent: Dec. 21, 1999

[54] METHODS FOR TREATING ARTHRITIS BY ADMINISTERING AN APOPTOSIS REGULATOR

[75] Inventors: Gary S. Firestein, Del Mar; Nathan J. Zvaifler, La Jolla; Douglas R. Green, San Diego, all of Calif.

[73] Assignee: The Regents of the University of California, Oakland, Calif.

[21] Appl. No.: 08/705,243

[22] Filed: Aug. 30, 1996

Related U.S. Application Data

[60] Provisional application No. 60/002,948, Aug. 30, 1995, abandoned, and provisional application No. 60/016,316, Apr. 26, 1996, abandoned.

[51] Int. Cl.$^6$ .............................. A61K 48/00; C12N 5/00; C12N 15/00
[52] U.S. Cl. ......................... 514/44; 435/320.1; 435/455
[58] Field of Search .......................... 514/44; 435/320.1, 435/455

[56] References Cited

PUBLICATIONS

Bandara et al., "Gene Transfer to Synoviocytes: Prospects for Gene Treatment of Arthritis", *DNA and Cell Biology*, 1992, vol. 11, No. 3, pp. 227–231.
Roessler et al., "Adenoviral–mediated Gene Transfer to Rabbit Synovium In Vivo", *Journal of Clinical Investigation*, Aug., 1993, vol. 92, pp. 1085–1092.
Firestein et al., "Apoptosis in Rheumatoid Arthritis Synovium", *Arthritis and Rheumatism*, Abstracts of Scientific Presentations, Sep. 1994, vol. 37, No. 9 (Supplement), p. s311, Abstract 899.
Anderson (Sep. 1995) Scientific Am. 124–126 and 128.
Verma et al (1997) Nature 389, 239–242.
*Science News Report* (1995) Science 269, 1050–1055.
Evans and Robbins, 1996, "Pathways to gene therapy in rheumatoid arthritis," *Curr. Opin. Rheumatol.* 8(3):230–4.
Makarov et al., 1996, "Suppression of experimenmtal arthritis by gene transfer of interleukin 1 receptor antagonists cDNA," *Proc. Nat'l. Acad. Sci.* 93(1):402–6.
Chernajovsky et al., 1995, "Inhibition of transfer of collagen–induced arthritis into SCID mice by ex vivo infection of spleen cells with retroviruses expressing soluble tumor necrosis factor recreptor," *Gene Ther.* 2(10):731–5.
Hanania et al., 1995, "Recent Advances in the Application of Gene Therapy to Human Disease," *Am. J. Med.* 99(5):537–552.
Evans and Robbins, 1995, "Progress toward the Treatment of Arthritis by Gene Therapy," *Ann. Med.* 27(5):543–546.
Zang et al., 1997, "Amelioration of Collagen–induced Arthritis by CD95 (Apo–1/Fas)–ligand Gene Transfer," *J. Clin. Invest.* 100(8):1951–1957.
Miagkova et al. (1998) Proceed. Natl. Acad. Sci. 95, 13859–13864.
Nita et al. (1996) Arthritis Rheum. 39, 820–828.

*Primary Examiner*—Deborah Crouch
*Attorney, Agent, or Firm*—Gray, Cary, Ware & Freidenrich, LLP; Lisa A. Haile, Ph.D.

[57] ABSTRACT

The present invention provides a novel method for the treatment of cellular accumulation in chronic inflammatory diseases such as rheumatoid arthritis. The method includes gene delivery and gene expression that is capable of enhancing apoptosis of accumulating cells and those cells which recruit accumulating cells. Also provided are diagnostic methods for detecting cellular accumulation diseases.

8 Claims, 5 Drawing Sheets

METHODS FOR TREATING ARTHRITIS BY ADMINISTERING AN APOPTOSIS REGULATOR

The present invention claims priority under 35 U.S.C. §119 from Provisional Application Ser. No. 60/002,948 filed Aug. 30, 1995, now abandoned, and from Provisional Application Ser. No. 60/016,316 filed Apr. 26, 1996, now abandoned, both of which are hereby incorporated herein in their entirety including all figures, drawings, graphs, illustrations, and equations. The present invention was made with Government support by National Institutes of Health Research Grant NIH 5 RO1 AR40525-04. The federal government may have certain rights to the invention.

FILED OF THE INVENTION

The present invention relates generally to programmed cell death (apoptosis) and more specifically to the diagnosis and treatment of diseases of excess cellular accumulation due to defective apoptosis and more specifically to diagnosis and treatment of rheumatoid arthritis.

BACKGROUND OF THE INVENTION

Rheumatoid arthritis is a chronic inflammatory arthritis that afflicts approximately 1% of adults (Mitchell, D. 1985. *Rheumatoid Arthritis*. P D Utsinger, N J Zvaifler, G E Ehrlich, eds. J.B. Lippincott Co., Philadelphia, pp. 133–150). The distribution of affected joints is symmetric and typically involves the small articulations of the hands and feet, although the larger appendicular joints like the shoulders and hips are often affected in established disease. Joint deformities, including ulnar deviation of the metacarpal phalangeal joints of the hand or destruction of the weight bearing joints, can occur late in the disease.

The symptoms of the disease result from a massive increase in the number of cells lining the synovium of the joint. The various cell types which are present include type A synoviocytes, which have the characteristics of monocytes or terminally differentiated macrophages, and type B synoviocytes which are fibroblast-like. As these cells increase in number, the continuous inflammation causes initial symptoms. Eventually, local release of enzymes by the synovial internal lining degrade the extracellular matrix and cause deformity.

The mainstays of therapy for rheumatoid arthritis include non-steroidal anti-inflammatory drugs, injectable gold salts, immunosuppressive agents, and methotrexate. While controlled studies do show some clinical benefit from these drugs, improvement is often limited and toxicity is common. Furthermore, most data suggest that these agents do not halt the rate of cartilage or bone destruction. Hence, a novel treatment that is directed at the pathogenesis of the disease with potential disease modifying activity would be a major improvement. The origin of the cells in the hyperplastic synovial lining in chronic inflammatory joint diseases remains controversial.

Necrosis and apoptosis are two basic processes by which cells may die. In necrosis cell death usually is a result of cell injury. The cells tend to swell and lyse, and the cell contents ultimately spill into the extracellular space. By contrast, apoptosis is a mode of cell death in which single cells are deleted in the midst of living tissues. Apoptosis accounts for most of the programmed cell death (PCD) in tissue remodeling and for the cell loss that accompanies atrophy of adult tissues following withdrawal of endocrine and other growth stimuli. In addition, apoptosis is believed to be responsible for the physiologic death of cells in the course of normal tissue turnover (i.e., tissue homeostasis) (Kerr, J. F., et al, 1972. *Br. J Cancer* 26: 239–257; Wyllie, A. H., et al. 1980. *Int. Rev. Cytol.* 68: 251–306).

The effector mechanisms of apoptosis are only incompletely understood, but the nuclear changes which occur appear to be caused by the activation of endogenous calcium-magnesium-sensitive nucleases that cleave chromatin between nucleosomes and reduce the DNA of apoptotic cells. A number of regulators of apoptosis have been identified. Some of these are already familiar as protooncogenes and oncosuppressor genes, including c-myc, bcl-2, p53, and ras. The protooncogene products and oncosuppressor proteins are believed to control cellular susceptibility to apoptosis (Isaacs, J. T. 1994. *Curr. Opin. Oncol* 6: 82–89). C-myc seems to determine whether cells continuously proliferate or enter apoptosis, depending on the availability of critical growth factors (Bisonnette, R. P., et al. 1994. In *Apoptosis II: The Molecular Basis of Apoptosis in Disease*. Cold Spring Harbor Laboratory Press). In cultured cells, expansion is usually determined by the presence of c-myc and growth factors, whereas apoptosis is seen when c-myc is present but growth factors are absent. Certain other oncogenes (e.g., ras and bcl-2) rescue cells from susceptibility to apoptosis. The oncosuppressor gene p53 is believed to initiate apoptosis by causing temporary G1/S arrest in cells expressing c-myc (Yonish-Rouach, et al. *Mol. Cell Biol.* 13: 1415–1423.).

SUMMARY OF THE INVENTION

The present invention is based on the seminal discovery that a causative agent of cellular accumulation in chronic inflammatory diseases is an insufficient level of apoptosis at the site of cellular accumulation. An insufficient level of apoptosis observed in these accumulation diseases correlates with the presence of altered or mutant polynucleotides or polypeptides known to be involved in apoptosis in the accumulating cells. Taken together, these findings indicate that the insufficient apoptosis among macrophages and fibroblast-like cells which causes the arthritis pathology or among other cells in chronic inflammatory diseases, is due to deficient apoptosis attributable to genes important in regulating apoptosis (e.g, p53).

Therefore, it is desirable to decrease the number of cells which may accumulate in chronic inflammatory disease by enhancing apoptosis at the site of increased cell number. Restoration of apoptosis may be accomplished by providing an apoptosis enhancing amount of functional or wild type gene, such as p53, to the tissues where cellular accumulation is occurring. Alternatively, specific therapy can provide a selective survival advantage only to cells that contain the wild type gene and gene product as opposed to a mutant or altered gene or gene product.

Other features and advantages of the invention will be apparent from the following description of the preferred embodiments thereof, and from the claims.

BRIEF DESCRIPTION OF THE DRAWINGS

FIG. 6A shows tissue stained with anti-CD68 antibody to detect macrophages. FIG. 6B shows tissue stained with anti-CD45RO antibody to detect memory T-cells.

DESCRIPTION OF THE PREFERRED EMBODIMENTS

Overview

Figure 1:
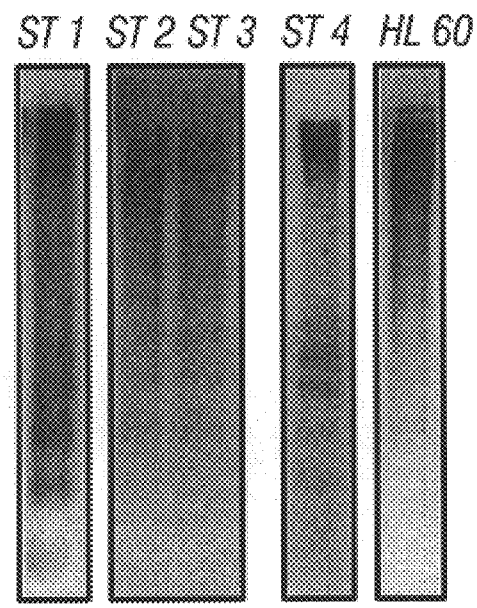
FIG. 1 shows evidence of apoptosis in the synovium of arthritis patients. A DNA ladder is readily visualized in extracted DNA from 4 synovial tissues. Actinomycin D-treated HL-60 cells are shown as a positive control (RA=ST 1, 3, 4; OA=ST 2). The figure shows a negative image of the ethidium stained gel.

Normal synovium is comprised of a superficial cellular layer made up of large cells with prominent interdigitating cytoplasmic processes. These cells form a lining 1–3 cells deep that rests on compact connective tissue bearing a vascular plexus and occasional cells. This superficial layer, which faces the joint cavity, is referred to as the synovial intimal or intimal lining (Harris, E. D., Jr. 1990. *N. Engl. J Med.* 322: 1277–1289; Zvaifler, N. J. and G. S. Firestein. 1994. *Arthritis Rheum.* 37: 783–789.). The lining is comprised of two types of synoviocytes that can be distinguished on morphologic, histochemical, and immunohistologic characteristics (Barland, P., et al. 1962. *J Cell Biol.* 14: 207–220.). The type A synoviocytes, which account for approximately one-third of the cell lining the normal synovium and as many as 80% of lining cells in rheumatoid arthritis, have the characteristics of monocytes or terminally differentiated resident tissue macrophages.

The remaining cells (type B synoviocytes) have morphologic features of fibroblasts with a regular membrane, limited numbers of filopodia, and large amounts of rough endoplastic reticulum, consistent with active metabolic processes. With inflammation, the synovial membrane becomes markedly expanded, edematous, and infiltrated with a variety of cells. As a part of this process, the lining cells become redundant, increase in number, and participate in the formation of villous projections. In addition, synovial lining cells increase many hundredfold.

In an attempt to discover the source of cellular accumulation in this disease process, rheumatoid arthritis and osteoarthritis synovial tissues were examined to determine if and where apoptosis occurs in situ. Genomic DNA extracted from rheumatoid arthritis synovium demonstrated DNA ladders characteristic of apoptosis. An in situ end labeling (ISEL) assay using digoxigenin-labeled nucleotides and alkaline phosphatase-labeled antibody identified DNA strand breaks in frozen synovial tissue sections from patients with rheumatoid arthritis (Wijsman, J. H., et al. 1993. *J. Histochem. Cytochem.* 41: 7–12). Although the number of DNA strand breaks we observed was increased in the synovial tissue from rheumatoid arthritis patients relative to normal and osteoarthritis controls, unexpectedly, a smaller than normal percentage of cells with DNA strand breaks were apoptotic. Apoptotic cells were primarily in the synovial lining and were predominantly macrophages, although fibroblast-like cells also had evidence of DNA fragmentation.

While not wanting to be bound by a particular theory, the following paradigm is believed to occur in cellular accumulation diseases such as rheumatoid arthritis. Synovial lining expansion occurs in the rheumatoid joint because of increased recruitment of macrophage-like and fibroblast-like cells and deficient apoptosis. Apoptosis of the synovial cells in rheumatoid arthritis appears to be an active process that involves both macrophage-like and fibroblast-like cells and is likely enhanced by the local cytokine milieu, regional production of reactive oxygen species, and intermittent ischemia and reperfusion in the joint. Despite the evidence for abundant DNA fragmentation consistent with apoptosis, it appears that this process is not rapid enough to maintain the normal synovial lining thickness since synovial lining expansion does, in fact, exist in rheumatoid arthritis. To account for this insufficiency of apoptosis, it is believed that the apoptosis pathway might be defective or aberrant and that cells with DNA strand breaks might either recover or persist for prolonged periods of time.

In attempting to define the source of such an apoptosis defect in rheumatoid arthritis, it was discovered that the p53 tumor suppressor plays a role in macrophage accumulation.

Using antibodies which specifically bind mutant p53 and wild-type p53 as well as cloning and sequencing of p53 genes, the present invention shows that mutant forms of p53 are expressed in the rheumatoid arthritis intimal lining. This result is surprising, since cell proliferation which normally occurs when altered p53 is present does not appear to significantly contribute to the increased number of cells in the joint. Detection of p53 using a pan-p53 antibody is, in and of itself, surprising given the fact that it is rarely observed in normal tissues due to its short half life (Reich, H. C., et al. 1983. *Mol Cell Biol.* 3: 2143–2150; Finlay, C. A., et al. 1988, *Mol Cell Biol.* 8: 531–539).

Moreover, the identification of a mutant apoptotic gene or deficient levels of apoptotic gene product has striking therapeutic implications. Given the abnormal accumulation of cells in the synovial lining, restoration or enhancement of wild type apoptotic protein production or selection for those cells expressing wild-type apoptotic genes will be beneficial by virtue of its ability to increase local lining apoptosis and thereby decrease the number of cells in the intimal lining. Since these are the cells that produce proteases and cytokines in rheumatoid arthritis, this will have a therapeutic benefit on the disease (Firestein, G S. *Rheumatology*. J Klippel and P Dieppe, eds. Gower Publications, London, 1994, pp. 3.12.1–30).

This approach may be generalized to other cellular accumulation diseases such as the arthritis diseases, including rheumatoid arthritis, seronegative spondyloarthropathies, ankylosing spondylitis, seronegative rheumatoid arthritis, psoriatic arthritis, juvenile rheumatoid arthritis, Reiter's Syndrome, arthritis associated with ulcerative colitis, Whipple's disease, arthritis associated with granulomatous ileocolitis, Behcet's disease, systemic lupus erythematosus, Sjogren's syndrome, mixed connective tissue disease; inflammatory lung disease such as asthma, bronchitis, sarcoidosis, and pulmonary fibrosis; neurological disease such as multiple sclerosis and ALS; as well as disorders such as inflammatory bowel disease, chronic graft rejection, glomerular nephritis, eczema, dermatitis, and the crystal induced arthritis conditions associated with pseudogout and hydroxyapatite.

The finding that cellular accumulation diseases are associated with defective or deficient apoptosis in genes such as p53, can be expanded to include other apoptotic genes, includes but not limited to as p21 Waf (Zakut and Givol, *Oncogene*, 11(2): 393, 1995), ras (Kinoshita, et al., *Oncogene*, 10(11): 2207, 1995), the bax family (Korsmeyer, S. J., *Trends in Genetics*, 11(3):101, 1995), and the ICE family (Fearnhead, et al., *Febs Letter*, 375(2): 303, 1995), for example. In general, mutations in apoptosis genes prevent cells from undergoing apoptosis (e.g., p53, ICE, p21Waf). It is believed that the presence of mutation inducing agents such as free oxygen radicals in the joint fluid for example, may contribute to mutations in genes such as apoptotic genes.

The invention also provides a diagnostic assay for rheumatoid arthritis and other cellular accumulation diseases.

The present invention provides a method for treating cellular accumulation in chronic inflammatory diseases, especially arthritis diseases such as those occurring in rheumatoid arthritis. In one embodiment a wild-type gene is provided to replace a defective apoptotic gene, to cells in the affected area in an expressible genetic construct such that endogenous production of the wild type protein in the region of cellular accumulation occurs. By using gene therapy to provide the wild type gene to accumulating cells, accumulating cells in the patient will increase endogenous production of wild type protein. This, in turn, will cause enhanced apoptosis, leading to a decrease in accumulation or an involution of the accumulating tissue. In the arthritis diseases, such as rheumatoid arthritis, providing wild type p53, for example, will result in subsequent prevention or improvement in the arthritic symptoms.

In rheumatoid arthritis, it is desirable to provide a wild type apoptotic gene to the accumulating macrophage cells as well as to any other cells in the region of accumulation which may also be accumulating, which may be involved in recruitment of macrophages to the diseased area, or which are otherwise contributing to the disease phenotype in the area of macrophage accumulation. Alternatively, it is desirable to specifically select those cells producing the wild type apoptotic gene. Both methods of treatment are discussed herein.

The invention also features a method for diagnosing cellular accumulation diseases by monitoring apoptotic polypeptide expression and a diagnostic kit for use with the diagnostic method.

Definitions

"Chronic inflammatory disease" or "cellular accumulation disease" means a disease in which an increased number of cells are found in a localized region of inflammation of the body. A patient with a cellular accumulation in chronic inflammatory disease may have multiple localized areas of cellular accumulation within the body. Preferably, the number of accumulated cells is increased at least 100% relative to the same tissue in an unaffected individual, more preferably, the increase is 2-fold, and even more preferably, the increase is 10-fold, or most preferably, at least 100 fold. The cellular accumulation in a chronic inflammatory disease is typically distinguished from a disease of cell proliferation by the fact that there are fewer than 1% mitoses relative to the same tissue in an unaffected individual.

Cellular accumulation in chronic inflammatory diseases include inflammatory diseases of the joint. For example, rheumatoid arthritis, seronegative spondyloarthropathies, ankylosing spondylitis, seronegative rheumatoid arthritis, psoriatic arthritis, juvenile rheumatoid arthritis, Reiter's Syndrome, arthritis associated with ulcerative colitis, Whipple's disease, arthritis associated with granulomatous ileocolitis, Behcet's disease, systemic lupus erythematosus, Sjogren's syndrome, mixed connective tissue disease, inflammatory bowel disease and the crystal induced arthritis conditions associated with pseudogout and hydroxyapatite all involve cellular accumulation within the joint area. The methods of the invention include the diagnosis and/or treatment of both symptomatic and asymptomatic individuals having cellular accumulation disease as well as diagnosis and/or treatment of those individuals having an increased likelihood of developing such a disease.

"Autoimmune disease" means a condition where the pathology is caused by increased destruction of host cells by the hosts immune system, e.g., rheumatoid arthritis, systemic lupus erythematosus, multiple sclerosis, Grave's disease, uveitis and sarcoidosis.

"Apoptosis-enhancing amount of apoptotic polypeptide" means an amount of polypeptide sufficient to enhance the percentage of cells undergoing apoptosis in a given population of cells known to undergo apoptosis such as type A and type B synoviocytes, relative to an untreated control cells of the same type. Preferably, the increase in apoptosis is at least 10%, more preferably at least 50%, and even more preferably, at least 5-fold, relative to an untreated control cell of the same type.

"Apoptosis", "apoptotic", or "apoptosis-associated" refers to the process of programmed cell death. Apoptosis-associated genes (and polypeptides) are associated with the regulation (enhanced or decreased) of the apoptosis phenomena in a cell.

"Apoptosis-regulating gene" ("apoptotic gene" or "apoptosis gene") means a gene which regulates (either enhances or inhibits) the process of apoptosis.

"Macrophage" means a cell of monocyte/macrophage lineage which expresses at least one of the macrophage markers provided herein. For example, type A synoviocytes are macrophage cells as are cells which express polypeptide to which anti-CD68 antibody binds specifically.

"Positioned for expression" means that the polynucleotide molecule is positioned adjacent to a polynucleotide sequence which directs transcription and translation of the sequence (i.e., facilitates the production of a p53 polypeptide, a recombinant protein, or a RNA molecule).

"Composition" means a formulation capable of gene delivery and gene expression, that is, capable of delivering a nucleotide sequence to, or directly into, a target cell whereupon the formulation containing the nucleotide sequence is incorporated on the cytoplasmic side of the outermost membrane of the target cell and capable of achieving gene expression so that detectable levels of gene expression of the delivered nucleotide sequence are expressed in the target cell. More preferably, after delivery into the cytoplasmic side of the cell membrane the compositon is subsequently transported, without undergoing endosomal or lytic degradation, into the nucleus of the target cell in a functional state capable of of achieving gene expression so that detectable levels of gene expression of the delivered nucleotide sequence are expressed in the target cell. Expression levels of the gene or nucleotide sequence inside the target cell are capable of providing gene expression for a duration and in an amount such that the nucleotide product therein is capable of providing a therapeutically effective amount of gene product or in such an amount as to provide a functional biological effect on the target cell. As used herein the term composition can refer to, but is not limited by, either explicitly or implicitly, the following examples: (1) liposomes or liposomal compositions both cationic and anionic in character and charge; (2) DNA or nucleic acid ionically complexed with a polycation/s and a ligand/s such that after attachment of the [DNA+Polycation+Ligand] composition to a cell surface receptor on a target cell via the ligand, the [DNA+Polycation+Ligand] composition is capable of being endocytosed into the target cell and the DNA is subsequently decoupled from the ligand and polycation and delivered to the cell nucleus in a functional condition for subsequent expression. Various alterations in the composition can be envisioned by those of ordinary skill in the art such as including peptide sequences which (a) prevent the composition from endosomal lysis after incorporation into the target cell by allowing the composition to leave the lysosomal vesicle, or (b) which act as a nuclear targeting agent chaperoning the nucleic acid through the nuclear pores and into the nucleus of the cell. Similar formulations are asialoglycoprotein-polylysine conjugation (Wu and Wu, *J. Biol. Chem.* 263: 14621, 1988; Wu et al., *J. Biol. Chem.* 264: 16985, 1989); (3) naked nucleic acid; (4) compacted nucleic acid; or (5) plasmid DNA which can be microinjected (Wolff et al., *Science* 247: 1465, 1990); (6) nucleic acid in a viral or retroviral vector compositions; and (7)colloidal dispersions (Felgner et al., *Proc. Natl. Acad. Sci. USA* 84: 7413, 1987; Ono et al., *Neuroscience Lett* 117: 259, 1990; Brigham et al., *Am. J. Med. Sci.* 298: 278, 1989; Staubinger and Papahadjopoulos, *Meth. Enz.* 101: 512, 1983). One of ordinary skill in the art will recognize that other compositions for the delivery of nucleotide sequences to target cells may be envisioned.

"Gene delivery" means transportation of a composition or formulation into contact with a target cell so that the composition or formulation is capable of being taken up by means of a cytotic process (i.e., pinocytosis, endocytosis, phagocytosis, ect.) into the interior or cytoplasmic side of the outermost cell membrane of the target cell where it will subsequently be transported into the nucleus of the cell in such functional condition that it is capable of achieving gene expression.

"Gene expression" means the process, after delivery into a target cell, by which a nucleotide sequence undergoes successful transcription and translation such that detectable levels of the delivered nucleotide sequence are expressed in an amount and over a time period that a functional biological effect is achieved. As used herein, gene expression can refer to but is not restricted by, either explicitly or implicitly, the following examples. A wild type p53 gene is delivered and expressed in targeted accumulating cells such that the targeted accumulating cells increase endogenous production of wild type p53 protein thus enhancing apoptosis and subsequently leading to a decrease in accumulation or an involution of accumulating tissue. For example, in diseases of arthritis, such as rheumatoid arthritis, delivery and expression of wild type p53 gene within target cells will result in subsequent prevention or improvement in arthritic symptoms due to a reduction in cell number after aptosis of the targeted cells. Gene therapy encompasses the terms gene delivery and gene expression.

"Expressible genetic construct" means a construct which has the p53 gene positioned for expression.

"Operably linked" means that a gene and a regulatory sequence(s) are connected to permit gene expression when the appropriate molecules (e.g., transcriptional activator proteins) are bound to the regulatory sequence(s).

"Mutant apoptotic" means an apoptotic gene or polypeptide (gene product), which has altered polynucleotide or polypeptide sequence or altered biological activity relative to wild-type apoptotic gene. For example, mutant p53 includes p53 which has increased stability and is therefore detectable when wild-type p53 is not detectable, and p53 with an altered immunogenicity is also mutant p53. Mutant apoptotic gene also includes polynucleotide sequences having a frameshift mutation, point mutation, missense mutation and the like.

"Apoptotic deficient" or "apoptotic defective" refers to the inability of an apoptosis-regulating gene or polypeptide to induce enhance or inhibit apoptosis, or cell death. Apoptosis as is known in the art is characterized by cell shrinkage, chromatin condensation, and DNA cleavage into nucleosomal fragments.

"Wild-type apoptotic" means a polypeptide with at least 70% of the biological activity associated with unaltered apoptotic polypeptide, and preferably, the wild-type polypeptide has at least 90% of the biological activity of unaltered polypeptide. The term "wild-type" similarly refers to the gene encoding the apoptotic polypeptide.

"Patient" or "subject" means a mammal, preferably a human, with cellular accumulation in a chronic inflammatory disease.

"Transformed cell" means a cell into which (or into an ancestor of which) has been introduced, by means of recombinant DNA techniques, a heterologons DNA molecule. Heterologous refers to a DNA sequence that either originates from another species or is modified from either its original form or the form primarily expressed in the cell.

"Transgene" means any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism. Included is a transgene created by the providing of an RNA sequence which is transcribed into DNA and then incorporated into the genome.

"Promoter" means the minimal nucleotide sequence sufficient to direct transcription. Also included in the invention are those promoter elements which are sufficient to render promoter-dependent gene expression controllable for cell-type specific, tissue specific, or inducible by external signals or agents; such elements may be located in the 5' or 3' regions of the native gene.

"Detectably-labeled" means any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}$P or $^{35}$S) and nonradioactive labelling (e.g., chemiluminescent labelling, e.g., fluorescein labelling).

"Purified antibody" means antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a p53 specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Fab' or (Fab')2 fragment, or a genetically engineered Fv fragment (Ladner et al., U.S. Pat. No. 4,946,788).

"Specifically binds" means an antibody which recognizes and binds a specified protein but which does not substantially recognize and bind other molecules in a sample, e.g., a biological sample, which naturally includes protein.

Abbreviations. ST=synovial tissue; DMEM=Dulbecco's modified Eagle's medium; FCS=fetal calf serum; FLS=fibroblast-like synoviocytes; ISEL=in situ end labeling; PCD=programmed cell death; act D=actinomycin D; NTB=nitroblue tetrazolium; BCIP=5-bromo-4-chloro-3-indolyl phosphate; MFC=mean fluorescence channel.

Defective Apoptotic Therapy

The present invention shows for the first time that mutations in apoptotic genes, such as p53, found in sites of cellular accumulation or inflammation, are somatic mutations, as evidenced by finding either no mutation in other tissues from the same patient, or finding different mutations in distinct or even the same samples from the same patient. The examples provided herein discuss mutations in the p53 apoptosis gene and production of a defective p53 polypeptide. It is understood that this is an exemplary model and that mutations in other apoptosis-regulating genes (e.g., bax, ICE) are amenable to detection and treatment of cells containing such mutant genes or gene products by the methods described herein.

Because the presence of mutant apoptosis polypeptide correlates with the excessive accumulation of cells due to insufficient apoptosis, the apoptotic gene finds use in gene therapy to enhance apoptosis for the treatment of cellular accumulation in chronic inflammatory diseases. This therapy is distinct from the use of such wild-type genes (e.g., p53) to decrease cell proliferation. In particular, to reduce the number of accumulating cells and surrounding cells that recruit cells accumulating to the diseased area, a functional wild-type gene may be introduced into cells at the sites predicted to require enhanced apoptosis such that the cells express a therapeutically effective amount of the gene product. In preferred therapies, the apoptosis-regulating gene product is preferentially expressed in those cells where enhanced apoptosis is required. Nucleotide sequences encoding p53, bax, ICE, ras, and p21 waf, for example, are well known to those of skill in the art. (Baker, et al. Science, 244: 217, 1989; Jenkins, et al., Nature, 312: 651, 1984; Zakut-Houri, et al., EMBO J. 4: 1251, 1985; Hesketh, The ONCOGENE Facts Book, Academic Press, p313, 1995; EP application 91307791.3). It is understood, however, that in some cases an apoptotic gene may also be associated with cellular proliferation. Alternatively, therapy can be provided by administration of peptidomimetic or other composition which mimics the biological activity of wild-type apoptosis polypeptides or which modifies the defect, such as a conformational defect, in the mutant apoptotic polypeptide to thereby restore the wild-type biological activity to the mutant polypeptide.

The preferred method of gene therapy is direct gene transfer, i. e., local application of the preparation containing the apoptotic polypeptide-encoding DNA into an afflicted joint or other region of cellular accumulation. In the case of rheumatoid arthritis, this allows targeting to the cells of the synovial intimal lining (e.g., the macrophage and fibroblast-like cells). A variety of well known vectors can be used to deliver the apoptosis-regulating gene to cells in a closed compartment like a joint, including but not limited to adenoviral vectors and adeno-associated vectors. In addition, naked DNA, liposome delivery methods, or other novel vectors developed to deliver the gene to cells can also be beneficial.

Any of a variety of promoters can be used to drive apoptosis-regulating gene expression, including but not limited to endogenous promoters, constitutive promoters (e.g., cytomegalovirus, adenovirus, or SV40), inducible promoters (e.g., a cytokine promoter such as the interleukin-1, tumor necrosis factor-α, or interleukin-6 promoter), and tissue specific promoters. In the case of rheumatoid arthritis, promoters for cytokine or metalloproteinase production or macrophage specific promoters (e.g., CD14 or CD68), or fibroblast specific promoters allow enhanced targeting to activated synoviocytes and leave normal resting cells unaffected.

Adenovirus, adeno-associated virus, herpes virus, vacciniavirus, retroviruses, or other viral vectors with the appropriate tropism for cells likely to require enhanced apoptosis (e.g., fibroblast-like synovial cells and macrophages) may be used as a gene transfer delivery system for a therapeutic apoptosis gene genetic construct. Viral vectors which do not require that the target cell be actively dividing, such as adenoviral and adeno-associated vectors, are particularly useful when the cells are accumulating, but not proliferative (as is the case with rheumatoid arthritis). Numerous vectors useful for this purpose are generally known (Miller, Human Gene Therapy 15–14, 1990; Friedman, Science 244: 1275–1281, 1989; Eglitis and Anderson, BioTechniques 6: 608–614, 1988; Tolstoshev and Anderson, Current Opinion in Biotechnology 1: 55–61, 1990; Sharp, The Lancet 337: 1277–1278, 1991; Cornetta et al., Nucleic Acid Research and Molecular Biology 36: 311–322, 1987; Anderson, Science 226: 401–409, 1984; Moen, Blood Cells 17: 407–416, 1991; and Miller and Rosman, Bio Techniques 7: 980–990, 1989; Le Gal La Salle et al., Science 259: 988–990, 1993; and Johnson, Chest 107: 77S–83S, 1995). Retroviral vectors are particularly well developed and have been used in clinical settings (Rosenberg et al., N. Engl. J. Med 323: 370, 1990; Anderson et al., U.S. Pat. No. 5,399,346).

By inserting an apoptosis-regulating gene sequence of interest into the viral vector, along with another gene which encodes the ligand for a receptor on a specific target cell, for example, the vector is now target specific. Viral vectors can be made target specific by attaching, for example, a sugar, a glycolipid, or a protein. Preferred targeting is accomplished by using an antibody to target the viral vector. Those of skill in the art will know of, or can readily ascertain without undue experimentation, specific polynucleotide sequences which can be inserted into the viral genome or attached to a viral envelope to allow target specific delivery of the viral vector containing the gene, e.g., the human wild-type p53 polynucleotide.

Since recombinant viruses are defective, they require assistance in order to produce infectious vector particles. This assistance can be provided, for example, by using helper cell lines that contain plasmids encoding all of the structural genes of the virus under the control of regulatory sequences within the viral genome. These plasmids are missing a nucleotide sequence which enables the packaging mechanism to recognize a polynucleotide transcript for encapsidation. These cell lines produce empty virons, since no genome is packaged. If a viral vector is introduced into such cells in which the packaging signal is intact, but the structural genes are replaced by other genes of interest, the vector can be packaged and vector virion produced.

Non-viral approaches may also be employed for the introduction of therapeutic apoptotic polynucleotide-encoding polynucleotide into cells otherwise predicted to undergo insufficient apoptosis. For example, p53 may be introduced into a macrophage, fibroblast, or other target cell type by the techniques of colloidal dispersion (Felgner et al., *Proc. Natl. Acad Sci. USA* 84: 7413, 1987; Ono et al., *Neuroscience Lett* 117: 259, 1990; Brigham et al., *Am. J Med. Sci.* 298: 278, 1989; Staubinger and Papahadjopoulos, *Meth. Enz.* 101: 512, 1983); asialorosonucoid-polylysine conjugation (Wu and Wu, *J. Biol. Chem.* 263: 14621, 1988; Wu et al., *J. Biol. Chem.* 264: 16985, 1989); or, less preferably, microinjection under surgical conditions (Wolff et al., *Science* 247: 1465, 1990).

Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules, RNA, DNA and intact virons can be encapsulated within the aqueous interior and be delivered to cells in a biologically active form (Fraley, et al., *Trends Biochem. Sci.,* 6: 77, 1981). In addition to mammalian cells, liposomes have been used for delivery of polynucleotides in plant, yeast and bacterial cells. In order for a liposome to be an efficient gene transfer vehicle, the following characteristics should be present: (Zakut and Givol, supra) encapsulation of the genes of interest at high efficiency while not compromising their biological activity; (Fearnhead, et al., supra) preferential and substantial binding to a target cell in comparison to non-target cells; (Korsmeyer, S. J., supra) delivery of the aqueous contents of the vesicle to the target cell cytoplasm at high efficiency; and (Kinoshita, et al., supra) accurate and effective expression of genetic information (Mannino, et al., *Bio Techniques,* 6: 682, 1988).

The composition of the liposome is usually a combination of phospholipid, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

For any of the above approaches, the therapeutic apoptotic polynucleotide construct is preferably applied to the site where the enhanced apoptosis is desirable (e.g., by injection), but may also be applied to tissue in the vicinity of the needed apoptosis event or even to a blood vessel supplying the cells where apoptosis is desirable.

In the gene delivery constructs of the instant invention, polynucleotide expression is directed from any suitable promoter (e.g., the human cytomegalovirus, simian virus 40, actin or adenovirus constitutive promoters; or the cytokine or metalloprotease promoters for activated synoviocyte specific expression). Furthermore, apoptotic polynucleotide production may be regulated by any desired mammalian regulatory element. For example, if desired, enhancers known to direct preferential gene expression in fibroblasts or macrophages may be used to direct apoptotic gene expression. Such enhancers include, without limitation, those enhancers which are characterized as tissue or cell specific in their expression.

Alternatively, if a apoptosis-regulating gene genomic clone is utilized as a therapeutic construct, expression is regulated by its cognate regulatory sequences or, if desired, by regulatory sequences derived from a heterologous source, e.g., any of the promoters or regulatory elements described above.

Less preferably, gene therapy is accomplished by direct administration of the apoptosis-regulating gene mRNA to a cell predicted to require apoptosis. This mRNA may be produced and isolated by any standard technique, but is most readily produced by in vitro transcription using a cDNA under the control of a high efficiency promoter (e.g., the T7 promoter). Administration of mRNA to accumulated cells is carried out by any of the methods for direct nucleic acid administration described above.

Ideally, the production of apoptosis protein by any gene therapy approach described above results in a cellular level of the apoptotic polypeptide that is at least functionally equivalent to the normal, cellular level in an unaffected individual. Treatment by any gene therapy approach may be combined with more traditional therapies.

Another therapeutic approach included within the invention involves direct administration of recombinant apoptotic protein, either to the site of cell accumulation or at the site where the accumulating cells originate (for example, by injection) or systemically by any conventional recombinant protein administration techniques. The actual dosage of protein depends on a number of factors, including the size and health of the individual patient, but, generally, between 0.1 mg and 100 mg inclusive are administered per day to an adult in any pharmaceutically-acceptable formulation.

In one embodiment, the invention provides a method of treating a patient having or at risk of having a cellular accumulation or a chronic inflammatory disease wherein the disease has an etiology associated with a defective apoptosis-regulating gene or polypeptide, the method comprising administering to the patient a therapeutically effective amount of a composition which modulates the expression of the apoptosis gene or polypeptide in an apoptosis defective cell such that the disease is ameliorated.

"Therapeutically effective" as used herein, refers to that amount of composition that is of sufficient quantity to ameliorate the cause of the cellular accumulation disorder. "Ameliorate" refers to a lessening of the detrimental effect of the disorder in the patient receiving the therapy. The subject of the invention is preferably a human, however, it can be envisioned that any animal with a cellular accumulation disorder can be treated in the method of the invention. The term "modulate" means enhance or inhibit expression of the apoptosis-regulating gene.

Therapeutic applications also include utilizing a selective survival technique taking advantage of those cells specifically expressing the wild-type protein, e.g., p53. Such treatment kills or inactivates the cell that contains a defective apoptosis gene, e.g., p53, while leaving cells containing the wild type or normal apoptosis gene/polypeptide unharmed. Several approaches for selective killing include but are not limited to: 1) infection with a viral vector to induce expression of the endogenous, normal apoptosis gene, e.g., p53; 2) contact a cell having a mutant apoptotic, e.g, p53, protein with an agent that specifically binds to the mutant and not the wild-type protein; and 3) contact a cell having a mutant apoptosis protein, e.g., p53 with a first agent that protects the wild-type p53 and then a second agent that is toxic to the mutant p53.

A function of the cellular phosphoprotein p53 is to inhibit the progression of mammalian cells through the cell cycle. Wild-type adenovirus Elb p55 protein binds to p53 in infected cells that have p53 and produce a substantial inactivation of p53 function, likely by sequestering p53 in an inactive form. Functional Elb p55 protein is essential for efficient adenoviral replication in cells containing functional p53. Hence, adenovirus variants which substantially lack the ability to bind p53 are replication deficient in cells having normal levels of functional p53.

In order for adenovirus to replicate efficiently in cells, the adenoviral Elb gene product, p55, forms a complex with the host cell p53 protein, thereby sequestering and/or inactivating p53 and producing a cell that is deficient in p53 function. Such a cell deficient in p53 function can support replication of the adenovirus. In this way, wild-type adenovirus is able to replicate in cells containing p53, as the adenovirus p55 proteins inactivates and/or sequesters the host cell p53 protein. In one embodiment of the invention, a recombinant adenovirus comprising an Elb locus encoding a mutant p55 protein that is substantially incapable of forming a functional complex with p53 protein in infected cells is administered to an individual or cell population comprising inflammatory cells capable of being infected by the recombinant adenovirus. The substantial incapacity of the recombinant adenovirus to effectively sequester p53 protein in infected cells expressing wild type p53 results in the introduced recombinant adenoviral polynucleotide(s) failing to express a replication phenotype in such cells. By contrast, cells which lack a functional p53 protein (apoptotic deficient or defective), support expression of a replication phenotype by the introduced recombinant adenovirus which leads to ablation of the apoptotic defective cell by an adenoviral cytopathic effect and/or expression of a negative selection gene linked to the replication phenotype. In preferred variations of these embodiments, the recombinant adenovirus comprises an Elb locus encoding a mutant p55 which is substantially incapable of binding p53 and may optionally also lack a functional p19 protein (i.e., incapable of inhibiting expression of adenoviral early region genes in the presence of Ela polypeptides). Recombinant adenoviruses used in the method of the invention may further comprise a mutant p19 gene which produces enhanced cytopathic effects; such a mutant known in the art is the p19 cyto mutant gene. However, it may be preferable to retain functional p19 in some mutants to maintain the integrity of viral DNA during the infection.

The invention also provides the use of recombinant papovaviruses, such as human papillomavirus (HPV), polyomaviruses (e.g., BK, JC) and SV40, which lack functional proteins for binding and/or inactivating p53 and cause selective ablation of apoptotic defective cells. Human papillomavirus mutants lacking expression of functional E6 protein will substantially lack the capability to effectively degrade p53 and thus will be capable of manifesting a replication phenotype in $p53^{(-)}$ (p53 mutant) cells but not in cells containing a sufficient level of functional p53.

As used herein, the term "replication deficient virus" refers to a virus that preferentially induces apoptosis in a predetermined cell population (e.g., cells substantially lacking p53 function) which supports expression of a virus replication phenotype, and which is substantially unable to induce apoptosis, or express a replication phenotype in cells comprising normal apoptotic function levels. Typically, a replication deficient virus exhibits a substantial decrease in plaguing efficiency on cells comprising normal p53 function.

As used herein, the term "p53 function" or "apoptosis polypeptide" function refers to the property of having an essentially normal level of a polypeptide encoded by the p53 or apoptosis gene (i.e., relative to apoptosis deficient cells of the same histological type) respectively, wherein the polypeptide is capable of binding an Elb p55 protein of wild-type adenovirus 2 or 5, for example.

Therefore, in one embodiment, an engineered adenoviral vector is used to treat patients with rheumatoid arthritis for example. As discussed above, cells that either lack the wild-type p53 or apoptosis protein or contain a mutant apoptosis protein cannot prevent adenoviral replication and are killed. Thus, in wild-type cells the infection is aborted. However, in cells that lack functional apoptosis protein, e.g., p53, the virus replicates, lyses the cell, and infects other cells until all of the p53-defective/mutant cells are killed. Thus this defective adenovirus is useful for purging a tissue of cells have apoptosis defective genes, e.g. p53. This approach is broadly applicable to selective killing of cells having other apoptosis-regulating genes which are defective. Preferably, the vector is administered systemically.

The second approach includes providing an agent that binds to the mutant apoptosis protein, e.g., p53, and is either directly toxic to cells or is conjugated to another agent that is toxic. For example, antibody PAb240 binds to mutant p53, but not wild-type, and therefore can be linked with a toxin, such as ricin. Such agents will be preferentially concentrated in cells containing mutant p53 and kill those cells.

A third approach is to administer an agent that binds to wild-type apoptosis polypeptide and not the mutant polypeptide, and protects the cells with wild-type apoptosis polypeptide from a second agent that is toxic to cells. Only cells containing mutant polypeptide, which is unprotected by the first agent, are susceptible to the second toxic agent. Apoptotic polypeptides such as p53 bind to various DNA motifs however the mutant polypeptide cannot bind to DNA. The sites on the apoptotic polypeptide that bind to the DNA motifs or other binding sites on the apoptotic polypeptide are useful for binding protective agents. All of these approaches and others are useful for targeting the mutant gene or protein to select specific cells for therapy that will kill or inactivate them.

Preventive Apoptotic Therapy

In a patient diagnosed as having or at risk of having a cellular accumulation disease due to chronic inflammation and who is producing insufficient or mutant apoptosis polypeptide or is susceptible to apoptosis-regulating gene mutations, even if those mutations do not yet result in alteration or loss of apoptosis polypeptide biological activity, any of the above therapies may be administered before the occurrence of the disease phenotype. For example, the therapies may be provided to a patient who has a family history of rheumatoid arthritis, but does not yet show accumulation of macrophages in the synovium. Gene therapy using a p53 expression construct, for example, may be undertaken to reverse or prevent the defects due to increased macrophage accumulation prior to the development of detectable levels of macrophage accumulation. Alternatively, the adenoviral vector described above is useful for preventative therapy.

Detection of Cellular Accumulation in Chronic Inflammatory Disease

Apoptosis polypeptide antibodies find diagnostic use in the detection or monitoring of conditions involving cellular accumulation. For example, the presence of mutant p53 may be correlated with enhanced macrophage accumulation in humans with rheumatoid arthritis (see the Examples below). Accordingly, detection of a decrease in the level of p53 protein or detection of the presence of a mutant p53 protein may provide an indication of a macrophage accumulation in this chronic inflammatory disease. Levels of p53 polypeptide may be assayed by any standard technique. For example, its expression in a biological sample (e.g., a biopsy) may be monitored, using standard direct or indirect immunoassay formats which are well known to those of skill in the art. Tissues which can be sampled are any of those believed associated with the particular disease such as synovial tissue or fluid, cerebrospinal fluid, colon biopsy, bronchoalveolar lavage, or lung biopsy, for example.

Alternatively, a patient sample may be analyzed for one or more mutations in the apoptosis-regulating gene sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant apoptotic gene detection, and each is well known in the art; examples of particular techniques are described, without limitation, in Orita et al., *Proc. Natl. Acad Sci. USA* 86: 2766–2770, (1989); and Sheffield et al., *Proc. Natl. Acad. Sci. USA* 86: 232–236, (1989). Of particular use are immunoassays to detect or monitor apoptotic protein in a biological sample enriched for macrophages relative to the tissues of the patient generally. Apoptotic protein-specific polyclonal or monoclonal antibodies (e.g., obtained as described below) may be used in any standard immunoassay format (e.g., ELISA, Western blot, or RIA assay) to measure apoptotic polypeptide levels, apoptotic polypeptide stability, or the presence of mutant apoptotic polypeptide; comparison is to wild-type apoptotic levels, and a decrease in apoptotic polypeptide or the presence of mutant apoptotic polypeptide are indicative of a condition involving macrophage accumulation. Examples of immunoassays are described, e.g., in Ausubel et al., *Current Protocols in Immunology*, Wiley Press, 1994.

In some embodiments, antibody to either mutant or wild type apoptosis polypeptide is used to diagnose rheumatoid arthritis using a biopsy sample obtained from the patient's synovial tissues. Immunohistochemical techniques may also be utilized for apoptosis polypeptide detection. For example, a tissue sample may be obtained from a patient, and a section stained for the presence of apoptotic polypeptide using an anti-apoptosis polypeptide antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra). Preferred antibodies are those which detect mutant p53.

In one preferred example, a combined diagnostic method may be employed that includes an evaluation of apoptotic protein production (e.g., by immunological techniques or the protein truncation test (Hogerrorst, F. B. L., et al., *Nature Genetics* 10: 208–212 (1995) and also includes a nucleic acid-based detection technique designed to identify more subtle p53 mutations (e.g., point mutations). As described above, a number of mismatch detection assays are available to those skilled in the art, and any preferred technique may be used (see above). By this approach, mutations in p53 may be detected that either result in loss of p53 expression or loss of p53 biological activity. In a variation of this combined diagnostic method, p53 biological activity is measured (e.g., assays for p53 activity).

Diagnostic assays also provide an opportunity to diagnose a predisposition to a cellular accumulation disease such as rheumatoid arthritis. For example, a patient heterozygous for an p53 mutation may show no clinical symptoms and yet possess a higher than normal probability of developing one or more types of macrophage accumulation diseases. Given this diagnosis, a patient may take precautions to minimize their exposure to adverse environmental factors, to carefully monitor their medical condition (e.g., through frequent physical examinations) or to have preventative therapy as described herein.

The diagnostic assays described above may be carried out using any biological sample from a patient with chronic inflammatory disease enriched for accumulating cells (e.g., any biopsy sample, bodily fluid, or tissue) in which the apoptotic gene is normally expressed (e.g., the cells from the synovial area). The diagnostic assays and kits of the invention provide that at least one apoptotic gene or polypeptide is detected. Therefore it is understood that a panel of apoptotic genes or polypeptides may be used for detection or diagnosis of a patient having or at risk of having a cellular accumulation disorder (e.g., a kit may detect p53, p21waf, ras, bcl2, etc.)

The antibody reactive with the apoptosis-regulating protein is preferably labeled with a compound which allows detection and quantitation of binding to the apoptosis protein. Any specimen containing a detectable amount of antigen or polynucleotide can be used, but preferably, the sample is enriched for accumulated cells. The level of apoptotic protein in the suspect tissue can be compared with the level in a normal tissue, in order to determine whether the subject has an apoptotic associated disorder. As mentioned above, one or more apoptotic gene products can be used for detection and diagnosis.

The invention also provides a method for detecting a cellular accumulation or chronic inflammatory disease associated with an apoptosis-regulating gene or gene product, e.g. p53 in a subject, comprising contacting a target cellular component containing the apoptotic gene or gene product with a reagent which detects the apoptosis gene or gene product and detecting the apoptotic gene or gene product. The target cell component can be nucleic acid, such as DNA or RNA, or protein. For example, a mutant apoptotic gene or gene product may be indicative of such a disorder. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the nucleic acid probe or antibody, or will be able to ascertain such, using routine experimentation.

For purposes of the invention, an antibody or nucleic acid probe specific for the apoptotic gene or gene product, e.g., p53, may be used to detect the presence of the apoptotic gene product (using antibody) or gene (using nucleic acid probe) in biological fluids or tissues, e.g., joint fluid. Oligonucleotide primers based on any coding sequence region in the Apoptotic gene or gene product sequence are useful for amplifying DNA, for example by PCR. Preferably the subject is human.

Alterations in an apoptotic gene or gene product nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Alterations in the apoptotic gene or gene product nucleic acid may be detected as a truncated or altered protein product. Such proteins can be analyzed by standard SDS-PAGE and/or immunoprecipitation analysis and/or Western blot analysis, for example. In addition, in vitro synthesized (IVS) protein assays can be used to analyze an apoptotic gene or gene product.

Disorders associated with apoptosis-regulating gene or gene product that are detectable by the method of the invention include those listed earlier, including rheumatoid arthritis.

In yet another embodiment, the invention provides a diagnostic kit useful for the detection of a target cellular component indicative of a cellular accumulation disease having an etiology associated with an apoptosis defective gene or polypeptide comprising carrier means and at least one container, wherein the first container contains at least one probe for detection of a mutation in an apoptotic nucleic acid or polypeptide. It is understood that the kit may contain a probe for one or more apoptotic genes or polypeptides, thereby allowing a panel to be screened at one time.

The following examples are intended to illustrate but not limit the invention. While they are typical of those that might be used, other procedures known to those skilled in the art may alternatively be used.

EXAMPLE I

Materials and Methods

Reagents

Reagents were obtained from the following sources: RNase A, DNase I, Klenow polymerase, dithiothreitol (DTT), digoxigenin-11-dUTP, anti-digoxigenin antibody conjugated to alkaline phosphatase, nitroblue tetrazolium (NTB), and 5-bromo-4-chloro-3-indolyl phosphate (BCIP) (Boehringer Mannheim, Indianapolis, Ind.); anti-bcl2 antibody, anti-CD68 antibody, anti-CD45RO antibody (DAKO Corp., Carpinteria, Calif.); proteinase K, actinomycin D, methyl green, tris base, boric acid, EDTA, sodium acetate, sodium chloride, ethidium bromide, agarose, collagenase (Sigma Chemical Col, St. Louis, Mo.); deoxynucleotide triphosphates (Pharmacia, Uppsala, Sweden); diaminobenzidene (DAB) (Research Genetics, Huntsville, Ala.); tritiated thymidine 5'-phosphate (30 Ci/mmole) (Amersham Corp., Arlington Heights, Ill.). All recombinant cytokines were purchased from Genzyme, Cambridge, Mass. (Recombinant hIL-1 beta (specific activity>$5\times10^7$ U/mg, purity>98%), rhIFN-gamma (spec. act. $2.5\times10^7$ U/mg, purity>99%) and rhTNF-alpha (spec. act. $2\times10^9$ U/mg, purity>98%)). Method for harvesting tissue DNA. About 100 mg of ST was lysed on ice for 30 min in STE plus 0.2% Triton-X. The nuclei were pelleted at 13,000×g at 4° C. for 15 min. The supernatant (containing low molecular weight DNA) was transferred to a fresh tube. RNase A (final concentration 50 ug/ml) was added to the supernatant and incubated at 37° C. for 1 h. Proteinase K (final concentration 100 ug/ml) was then added and incubated for an additional 4 h at 50° C.

The DNA was extracted with phenol/chloroform twice and precipitated from the aqueous phase overnight after the addition of 0.1 vol of 3 M sodium acetate and 2.5 vol 100% EtOH. DNA was recovered by centrifugation at 13,000×g at 4° C. for 20 min and washed once with 70% EtOH. The DNA pellet was resuspended in Tris-EDTA buffer. 5–15 ug of DNA from each sample was subjected to electrophoresis on 1.5% agarose gel containing ethidium bromide and visualized under UV illumination.

In situ End Labeling (ISEL) Assay

Fragmented DNA was detected in cell nuclei using a modification of previously described methods (Wood et al., *Neuron.*, 11: 621–32, 1993 and Wijsman et al., *J. Histochem. Cytochem.* 41: 7–12, 1993). Frozen section of synovial tissue (5–6 microns thick) were placed onto poly-L-lysine coated slides and air dried for at least 2 hours. The tissue sections were then fixed with EtOH/Acetic acid 3:1 for 10 min at room temperature and washed with buffer 1 (see below) for 5 min. The slides were then air dried for at least 2 h. 10–15 ul of DNA polymerase mix were added to each section and incubated at room temperature for 1 h. The sections were washed with buffer 1 (see below) for 5 min at room temperature followed by a wash in buffer 2 for 5 min.

Alkaline phosphatase conjugated anti-digoxigenin antibody was diluted to 1:500 in buffer 2 and 15–20 ul was applied to each specimen. The slides were incubated at 37° C. for 2 hrs in a humidified chamber and then washed with buffer 1 for 5 min. They were then equilibrated with buffer 3 for 5 min and the color reagent (NBT+BCIP) was added to the specimens. After about 30 min the slides were washed with distilled water, counterstained with eosin or methyl green and dehydrated with graded alcohol washes. The developing reagent gave a dark purple color for positive signals. Buffers:10X DNA polymerase buffer=0.5M Tris.Cl pH7.5, 0.1M MgCl2, 1 mM DTT; 10X nucleotide mix=1 mM each of dATP, dCTP and dGTP, 0.4 mM dTTP; DNA polymerase mix=10X DNA pol buffer (2 ul), 10X nucleotide mix (2 ul); 100 µM dig-11-dUTP (0.5 ul), Klenow polymerase (2 ul (2 U)), Water (13.5 ul); Buffer 1=100 mM Tris.Cl pH7.5, 150 mM NaCl; Buffer 2=0.5% Blocking agent in buffer 1, Buffer 3=100 uM TrisHCl pH 9.5, 100 uM NaCl, 50 uM MgCl2. Quantification of ISEL assay. A semiquantitative scale was used to estimate the degree of ISEL staining in tissue sections that had been counterstained with methyl green to distinguish ISEL-positive and -negative cells. Four areas were reviewed by a blinded investigator: the synovial intimal lining, the sublining, blood vessels, and lymphoid aggregates. The extent of staining in the area was estimated and scored as using a previously established semiquantitative scale.

Synovial Tissue

Synovial tissue was collected at the time of total hip or knee replacement from patients with osteoarthritis or rheumatoid arthritis (Alvaro-Gracia, et al., *J. Clin. Invest.*, 86: 1790–8, 1990). One rheumatoid arthritis tissue was obtained by percutaneous synovial biopsy as previously described (Firestein, et al., *Arthritis Rheum.* 37: 193–200, 1994). Four normal synovial tissues were harvested post-mortem from patients without previous history of arthritis. The post-surgical specimens were placed on ice and subsequently snap frozen within 1 h. The post-mortem specimens were processed within 6–12 hours after death.

Synoviocyte Culture

Synovial cells were isolated by enzymatic dispersion of synovial tissues as previously described (Alvaro-Gracia, et al., supra). Briefly, the tissues were minced and incubated with 1 mg/ml collagenase in serum-free DMEM (Gibco, Grand Island, N.Y.) for 2 h at 37° C., filtered through a nylon mesh, extensively washed, and cultured in DMEM supplemented with 10% fetal calf serum (FCS) (Gibco, endotoxin content<0.006 ng/ml), penicillin, streptomycin, and L-glutamine in a humidified 5% $CO_2$ atmosphere. After overnight culture, non-adherent cells were removed and adherent cells were cultivated in DMEM plus 10% FCS.

At confluence, cells were trypsinized, split at a 1:3 ratio, and recultured in medium. Synoviocytes were used from passages 3 through 9 in these experiments, during which time they were a homogeneous population of fibroblast-like synoviocytes (FLS)(<1% CD11b, <1% phagocytic, and <1% Fc-gamma RII receptor positive).

Immunohistochemistry in Combination with ISEL

Because anti-CD68 and -CD45RO antibodies did not bind to ethanol:acetic acid treated sections, double staining studies were performed on acetone fixed tissue (5 min at 4° C.). This fixative optimized immunoperoxidase staining, although the ISEL signal was not as well localized to nuclei (perhaps due to leaching of DNA fragments into the cytoplasm). The ISEL procedure was then performed as above. However, before addition of anti-digoxigenin antibody, standard immunohistostaining was performed. The primary antibody (anti-bcl2, -CD68, or -CD45RO) was added for 60 min at room temperature. The control MAb was an isotype matched control at the same concentration. After 2 washes in PBS plus 0.1% BSA, biotinylated horse anti-mouse antibody (Vector Laboratories, Inc., Burlingam, Calif.) in 10% human AB serum was added for 30 minutes. The slides were washed and endogenous peroxidase was depleted with 0.3% hydrogen peroxide in PBS for 15 min. The slides were then washed extensively, incubated with ABC horseradish peroxidase complex (Vector Laboratories, Inc.) for 30 minutes, and developed with DAB. After this step, the anti-digoxigenin antibody was added and the ISEL assay was completed as above. The double-stained slides were counterstained with either eosin or 0.1% methyl green.

Additional Immunohistochemistry

Fixed, permeabilized sections of RA, OA, and other non-inflammatory synovial tissues (ST) were probed using the monoclonal antibody PAb 1801 which binds p53 intracellularly in situ. Virtually all RA tissues stained intensely in the synovial intimal lining (see Table 1). Most often, the layer of cells in direct contact with the intra-articular space (and synovial fluid) was positive. The p53 protein was detected in both the cytoplasm and nuclei of lining cells, although cytoplasmic staining tended to be more prominent in the intimal lining while nuclear staining occurred more often in the sublining layer. Lesser amounts of immunoreactive p53 were detected in the sublining mononuclear cells. Occasional positive cells were identified within lymphoid aggregates, but the majority of p53-expressing sublining cells were scattered throughout the sublining or clustered around blood vessels.

Samples from non-RA synovia were also examined. The OA ST (n=5) samples also contained immunoreactive p53. As with RA samples, the primary site was in intimal lining, although the amount of staining was significantly less than rheumatoid tissues ($p \leq 0.05$; see Table 1). Minimal or no staining was observed in 3 non-inflammatory ST (normal, post-traumatic arthritis, and avascular necrosis) ($p \leq 0.05$ compared with RA; see Table 1).

TABLE 1

Expression of immunoreactive p53 in synovium

| | Lining | Sublining mononuclear cells | Inflammation score |
|---|---|---|---|
| RA = (n = 9) | 2.9 ± 0.3* | .9 ± 0.2 | 6.0 ± 0.5* |
| OA = (n = 5) | 1.8 ± 0.4 | .04 ± 0.2 | 2.6 ± 0.2** |
| Non-inflammatory (n = 3) | 0.7 ± 0.3 | 0.3 ± 0.3 | 1.3 ± 0.3 |

*$p \leq 0.05$ compared with OA or non-inflammatory ST;
**$p \leq 0.03$ compared with non-inflammatory ST; #1 normal, 1 avascular necrosis, 1 post-traumatic.
Semi-quantitative scales for staining and inflammation are as described in methods.

Western Blot Analysis

To confirm the presence of immunoreactive p53 in RA ST, western blot analysis was performed on extracts of synovial tissue that had been snap frozen immediately after removal from the joint. Prominent p53 bands were observed in the lanes containing RA extracts. Of the 8 RA ST examined by western blot analysis, 7 contained significant amounts of immunoreactive p53 protein. Control antibodies did not exhibit binding at 53 kD (data not shown). Four RA ST were enzymatically digested and extracts were prepared from the adherent cell population. This population is comprised of fibroblast-like synoviocytes and macrophage-like synoviocytes but is devoid of lymphocytes. In each case, the immunoreactive p53 was detected. Six OA ST extracts were also examined. Four were negative and 2 contained faint bands, a finding that is consistent with the immunohistochemistry data as presented in Table 1.

$^3$HdTr Nuclear Fragmentation Assay

Rheumatoid arthritis FLS were seeded at $10^4$ cells/well in a 96-well microtiter plate. The cells were cultured at 37° C. and 5% $CO_2$ for 2 days. On the third day, 10 uCi/ml/well of 3HdTR was added to each well and incubated overnight. The cells were then treated with different concentrations of cytokines or antibodies for 8 h or actinomycin D (act D) for 4 h and then lysed by 2 rounds of freeze-thaw cycles. Lysed cells and media were aspirated onto fiber glass filters using a cell harvester. The filters were washed to remove unincorporated nucleotides and counted in a liquid scintillation counter. All points were done in triplicates. Percent specific fragmentation was calculated as follows: $(S-E) \times 100/S$, where E=retained cpms on the filter in the presence of cytokine and S=retained cpms on the filter in the medium control (Matzinger, P., J. Immunological Methods 145: 185–92, 1991). A high percent of specific fragmentation indicates that DNA was incorporated into low molecular weight fragments that were not retained on the filter.

FACS Analysis

FLS (1–2 x105) were cultured in 6-well plastic dishes (Costar, Cambridge, Mass.) in DMEM-10% FCS. Cells were harvested with 5 mM EDTA at 4° C. and stained with anti-fas or control antibody (Kamiya Biomedical Co., Thousand Oaks, Calif.) as previously described (Alvaro-Gracia, et al., supra). Phycoerythrin conjugated Fab2 anti-mouse IgG (Tago Inc. Burlingame, Calif.) was used as a secondary antibody. An isotype matched MAb was used as negative control. Induction of Fas expression by cytokines was calculated from the mean fluorescence channels (MFC) as follows: relative MFC=(MFCcytokine-MFCIgG)/(MFCmedium-MFCIgG). A cell was defined a positive if its MFC was greater than 98% of cells stained with the control antibody. Statistical analysis. Data were analyzed using the paired Student t test and are presented as mean+SEM.

EXAMPLE II

Rheumatoid Arthritis Synovium Contains Fragmented DNA

Initial studies were performed to determine if DNA isolated from rheumatoid arthritis synovium contained nucreosomal DNA. Low molecular weight DNA was isolated from whole synovial tissue extracts and separated by agarose gel electrophoresis. Six tissues processed were in this manner (5 rheumatoid arthritis and 1 osteoarthritis) and each showed the characteristic DNA ladder observed in apoptosis (see FIG. 1 for representative examples).

EXAMPLE III

In situ Detection of DNA Fragmentation

To determine which cells contained fragmented DNA in synovial tissue, an in situ end labeling (ISEL) assay was used. 12 rheumatoid arthritis, 4 osteoarthritis, and 4 normal synovia were studied.

Figure 2:
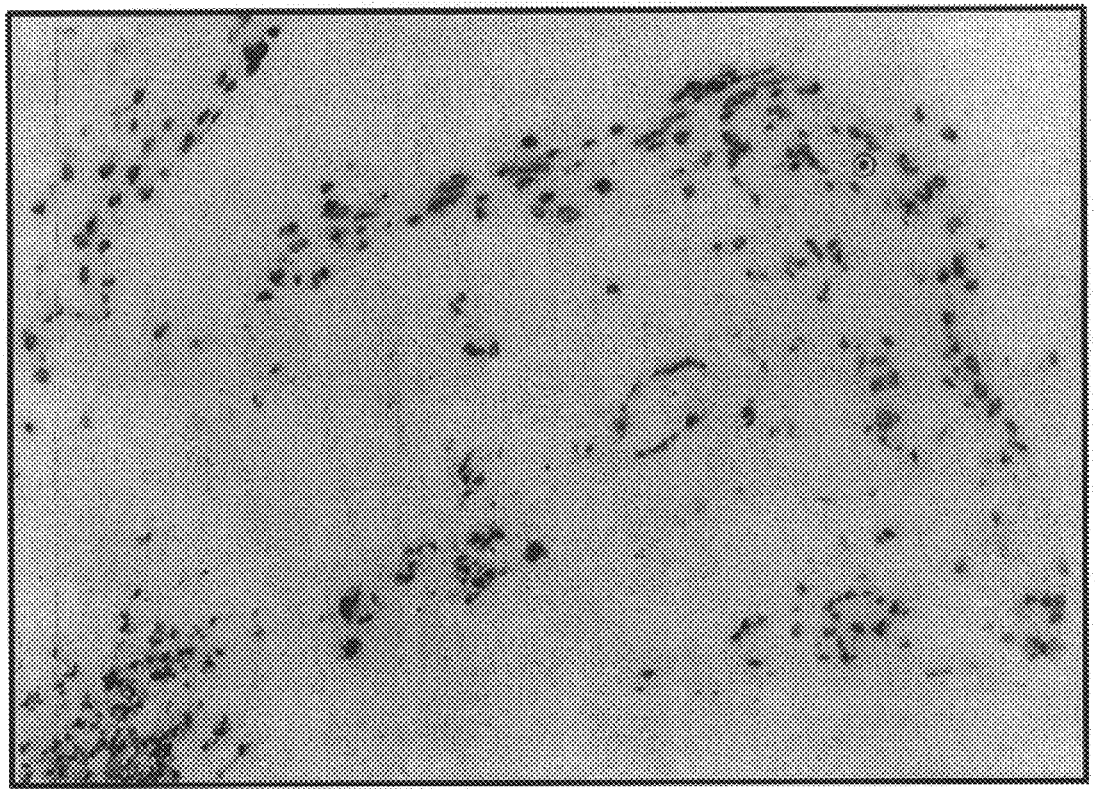
FIG. 2 shows an in situ end labeling (ISEL) assay on frozen sections of rheumatoid arthritis synovial tissue to demonstrate DNA strand breaks. Tissues were counterstained only with eosin, so that normal nuclei are not visualized. Nuclei with fragmented DNA (dark nuclei) are readily distinguished in the intimal lining.

All arthritis tissues but only 2 of the 4 normal specimens were positive (i. e., >5% positive cells). FIG. 2 shows a representative example of an rheumatoid arthritis tissue. Many cells with DNA strand breaks were located in the synovial intimal lining, varying from rare positive cells to >50% positive. The amount of apoptosis was significantly greater in rheumatoid arthritis lining and sublining compared with osteoarthritis and normal synovium (see Table 2).

TABLE 2

Location of Apoptotic Cells in Synovial Tissue

|  | Intimal lining | Sublining | Blood vessels |
|---|---|---|---|
| RA (n = 12) | 2.6 ± 0.1 | 2.0 ± 0.2 | 0.8 ± 0.2 |
| OA (n = 4) | 1.7 ± 0.5* | 1.0 ± 0.4* | 0.5 ± 0.3 |
| Normal (n = 4) | 1.0 ± 0.4* | 1.0 ± 0.4* | 0.3 ± 0.2 |

0 = negative; 1+ = rare positive cells in a specific region; 2+ = scattered clusters of positive cells in a specific region; 3+ = moderate staining in a specific region; 4+ = extensive staining in a specific region.
*$p < 0.05$ compared to rheumatoid arthritis A potential concern about the ISEL studies is that DNA strand breaks might actually occur ex vivo (after surgery and prior to snap freezing). To address this possibility, a percutaneous synovial biopsy from an rheumatoid arthritis patient was examined using ISEL. That tissue was also ISEL-positive, and staining was equivalent to most other rheumatoid arthritis tissues even though it was processed and frozen within a minute of procurement. In a separate experiment, a portion of one rheumatoid arthritis synovium obtained at joint replacement surgery was snap frozen within 20 min after removal from the joint while a second block from the same tissue was maintained at room temperature for 2 h. Frozen sections of both blocks were subsequently studied using the ISEL technique and showed equivalent degrees of staining. Taken together, these experiments strongly suggest that the data obtained with surgical specimens reflects the situation in vivo.

EXAMPLE IV

Identification of Cells Containing Fragmented DNA

Figure 6A:
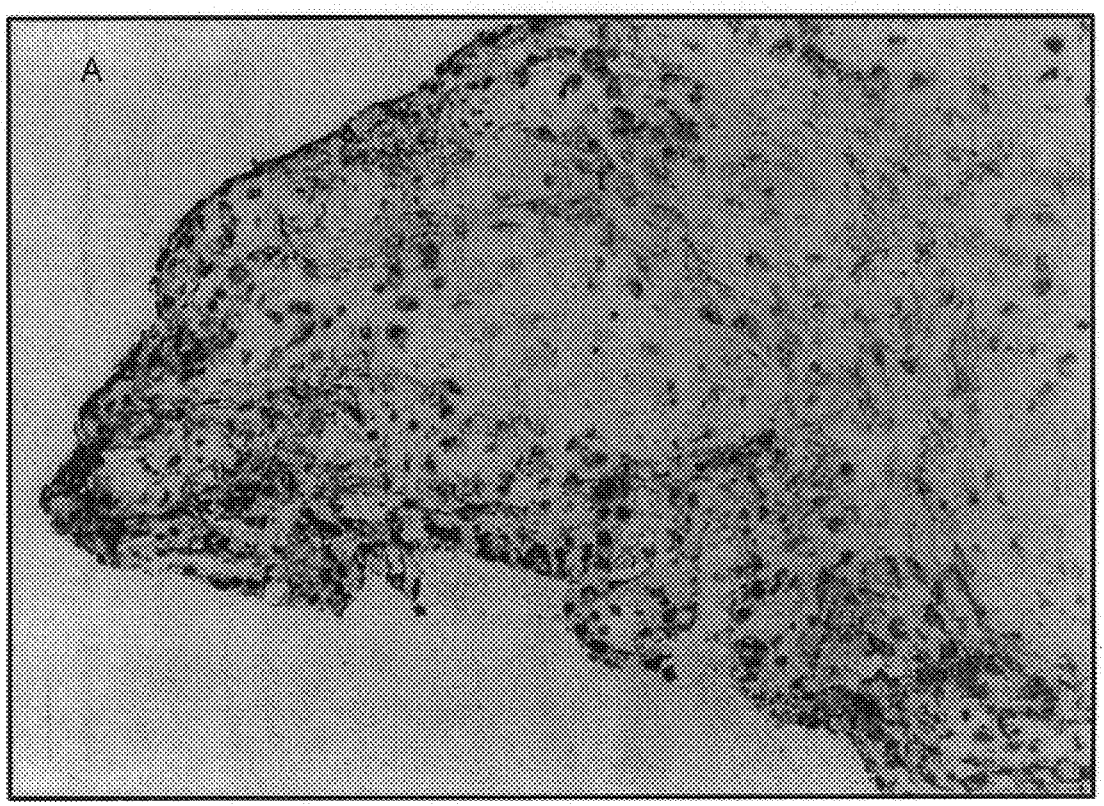
FIGS. 6A and 6B show a combination immunohistochemistry and ISEL. Tissues are counterstained with methyl green to show ISEL-negative nuclei. (Brown color= immunoperoxidase stain for cell surface markers; dark purple color=ISEL-positive nuclei; light turquoise color= methyl green stain of ISEL-negative nuclei)
Figure 6B:
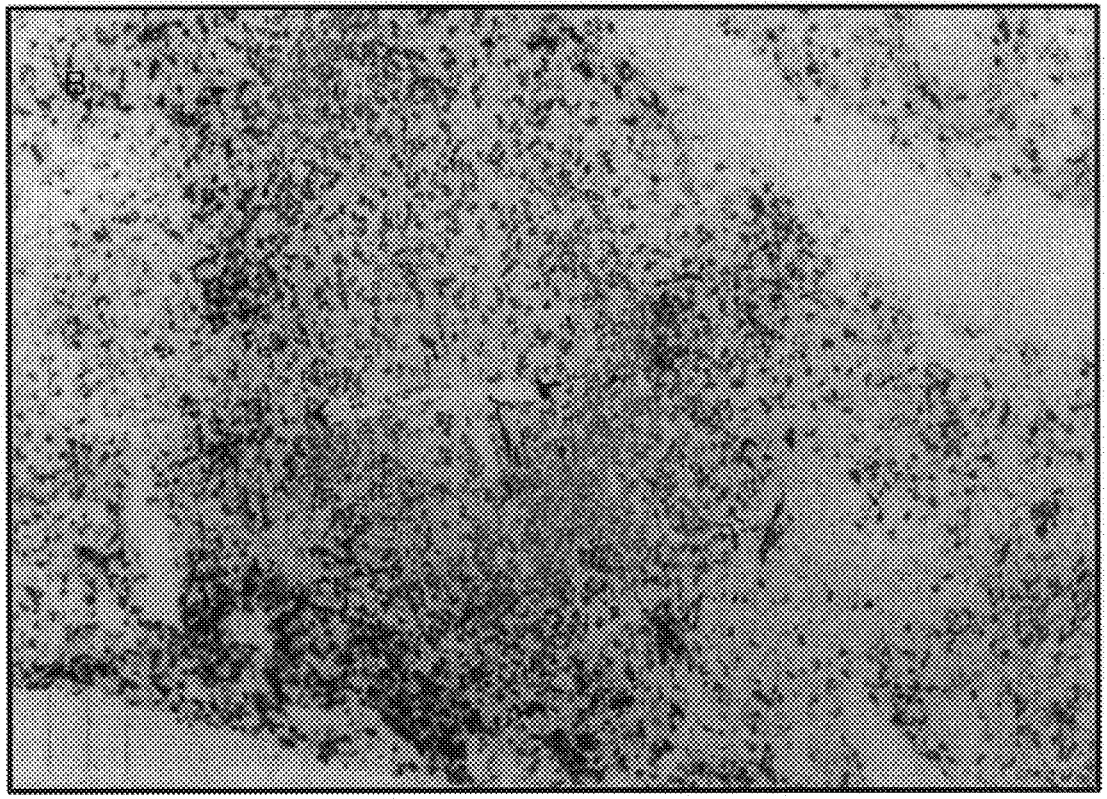

Immunohistochemistry was combined with ISEL to determine the phenotype of apoptotic cells. As shown in FIG. 6A, cells expressing the macrophage antigen CD68 constituted the majority of the ISEL-positive cells in the intimal lining, especially in the most superficial layer. The presence of some CD68-negative/ISEL-positive cells in the lining suggested that FLS had DNA strand breaks consistent apoptosis. A regular finding, as noted above, was the lack of ISEL staining of CD45RO-positive T cells in lymphoid aggregates, even though ISEL-positive cells frequently surrounded the aggregates (FIG. 6B).

Some individual CD45RO-negative/ISEL-positive cells were scattered throughout the sublining, suggesting that only the T cells in aggregates were protected from apoptosis.

The most striking evidence for DNA strand breaks in rheumatoid arthritis was in the synovial intimal lining, which is comprised of macrophage-like and fibroblast-like synoviocytes. Increased numbers of both cell types contribute to lining hyperplasia in rheumatoid arthritis, but the percent change in macrophages is thought to be greater. DNA fragmentation was readily detected in this region using the ISEL assay, but the amount of PCD was surprising in light of the previous hypothesis that apoptosis might be low in inflamed synovium (Mountz, et al., *Arthritis Rheum.* 37: 1415–1420, 1994). The majority of cells with DNA strand breaks in the lining were CD68-positive macrophages. These terminally differentiated cells are derived from the bone marrow and migrate through the blood stream to the synovium (Mapp, et al., *Rheumatol. Intl.* 8: 171–6, 1988). However, fibroblast-like cells of the synovium also exhibited DNA strand breaks. While little is known about the dynamics of this process, our data suggest that significant turnover occurs and that the lining is continuously repopulated with less mature macrophages. This relative age of mononuclear phagocytes could have a profound influence on the synovial cytokine profile, since younger macrophages are more likely to produce pro-inflammatory cytokines like IL-1 while mature cells are biased towards anti-inflammatory cytokines like IL-1ra (Arend, et al., *J. Immunol.* 147: 1530–6). The replacement of senescent macrophages by younger ones could help explain the relative defect in IL-1ra production and the overproduction of IL-1 by synovial macrophages (Firestein, et al., *Arthritis Rheum.* 37: 644–52, 1994).

EXAMPLE V

ISEL-Negative Cells in Lymphoid Aggregates Express bcl2

Figure 7:
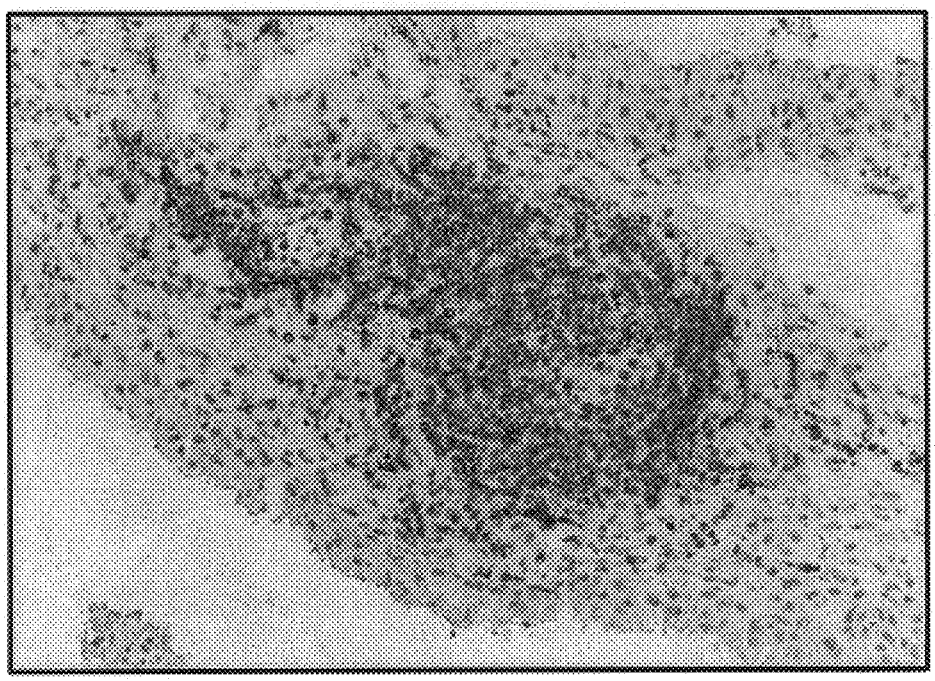
FIG. 7 shows immunochemistry showing bcl2 expression is prominent in lymphoid aggregates, but is minimal in the intimal lining.

Because T cells in lymphoid aggregates showed little evidence of DNA fragmentation, immunohistochemistry was performed to determine if they expressed the oncogene bcl2, which protects cells from apoptosis (Itoh, et al, *J. Immunol.* 151: 621–7 1993; Korsmeyer, S. J., Blood, 80: 879–86, 1992; Hockenbery, et al., *Cell,* 75: 241–51, 1993). Bcl2 expression was low or absent in some tissues, but, when present, it was primarily found in sublining lymphoid aggregates (see FIG. 7).

EXAMPLE VI

Apoptosis in cultured Fibroblast-like Synoviocytes

Figure 8:
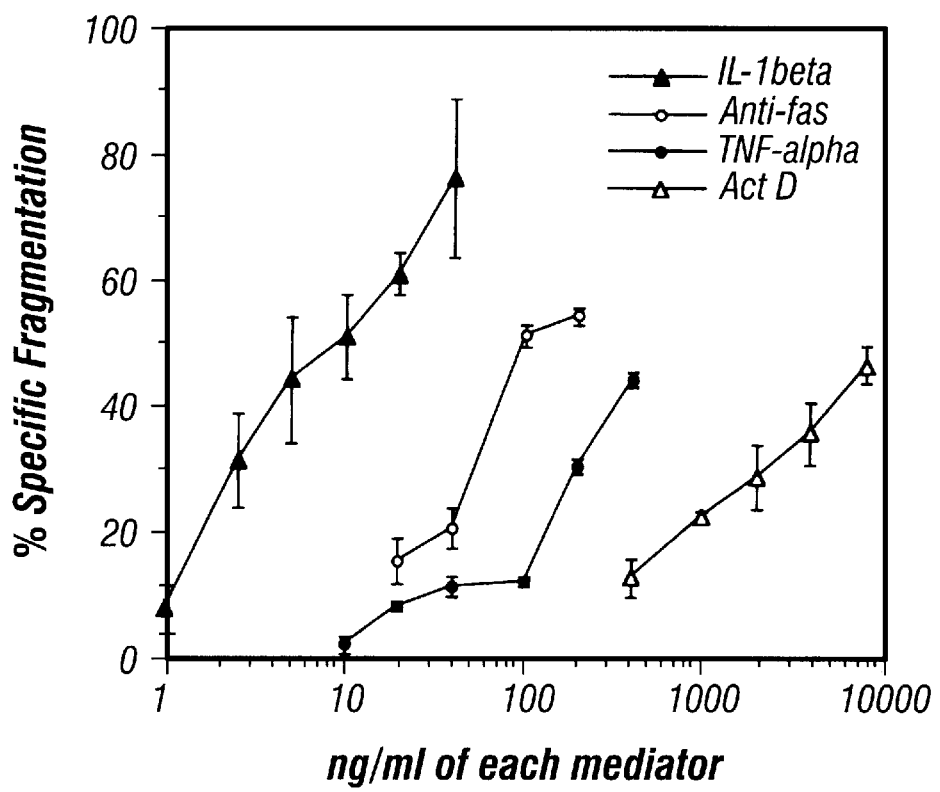
FIG. 8 shows DNA fragmentation in FLS. Cells were treated with various concentrations of act D, anti-fas antibody, IL-1 beta, or TNF-alpha and the extent of DNA fragmentation was determined by tritiated thymidine incorporation.

The presence of CD68-negative apoptotic cells in the synovial lining prompted an analysis of the regulation of FLS apoptosis in vitro. Using the ISEL assay on resting FLS cultured in chamber slides, apoptosis was shown to be very low. IFN-gamma alone had a minimal effect, while anti-fas antibody, IL-1 beta, TNF-alpha, and act D caused significant DNA fragmentation (see Table 3). Osteoarthritis and rheumatoid arthritis-derived FLS were equally susceptible to induction of DNA strand breaks. IFN-gamma in combination with these factors significantly reduced FLS apoptosis, while TNF-alpha was additive with actinomycin D. To confirm the effect of each apoptosis-inducing factor, a second assay ($^3$HdTr nuclear fragmentation) was used to quantify DNA fragmentation in cultured FLS. As with the ISEL method, this technique showed that anti-fas, IL-1beta, TNF-alpha, and actinomycin D each caused DNA fragmentation (see FIG. 8).

TABLE 3

Apoptosis in cultured fibroblast-like synoviocytes

| Condition | % apoptotic cells With IFN-gamma | Without IFN-gamma(100 U/ml) |
| --- | --- | --- |
| Medium | 3 ± 1 | 6 ± 2 |
| IL-1 (1 ng/ml) | 50 ± 2 | 30 ± 2* |
| TNF-alpha (100 ng/ml) | 35 ± 1 | 23 ± 2** |
| Actinomcyin D (0.5 ug/ml) | 37 ± 5 | 16 ± 3** |
| Act D + TNF-alpha | 56 ± 3 | N.D. |
| Act D + IL-1 | 56 ± 5 | N.D. |
| anti-fas antibody (80 ng/ml) | 42 ± 5 | N.D. |

FLS were incubated with mediators for 16 h (n = 3 separate experiments) in the presence or absence of 100 U/ml of IFN-gamma. DNA fragmentation was determined with the ISEL assay.
*p = 0.057 compared to IL-1 alone; **p < 0.03 compared to TNF-alpha or act D alone; N.D. = not done

EXAMPLE VII

Surface Fas Expression on FLS

Figure 9:
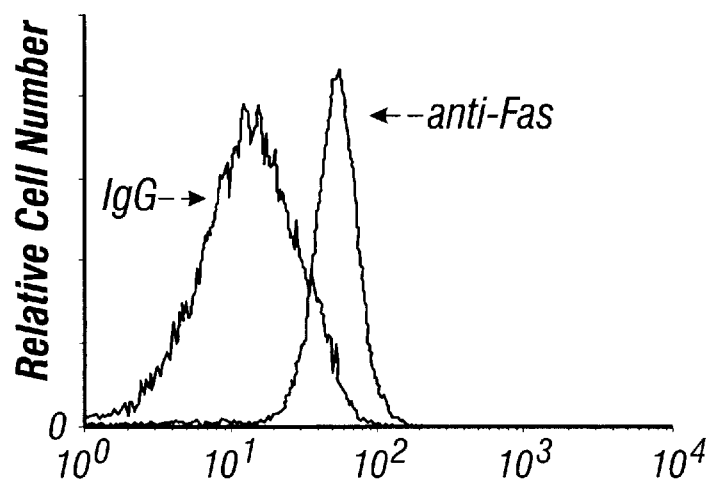
FIG. 9 shows a histogram from a representative experiment demonstrating fas expression on FLS. The vertical axis shows relative cell number and the horizontal axis shows relative red fluorescence. Cells were stained with either anti-fas antibody or control antibody.

Since anti-fas antibody induced DNA fragmentation in FLS, fas expression was determined on these cells using flow cytometry. Many FLS constitutively expressed Fas protein on the cell surface (see FIG. 9 for a representative experiment (n=7; 4 rheumatoid arthritis and 3 osteoarthritis)). There were no significant differences between osteoarthritis and rheumatoid arthritis FLS with regard to the level of surface Fas expression on resting synoviocytes. To determine if key cytokines present in inflamed synovial tissue could regulate fas expression, six of the FLS lines (3 rheumatoid arthritis and 3 osteoarthritis) were cultured with IL-1beta (1 ng/ml) or TNF-alpha (100 ng/ml) for 16 to 24 hours. The results for osteoarthritis and rheumatoid arthritis FLS were similar and were pooled. As shown in Table 4, TNF-alpha significantly increased surface Fas expression at both time points. Although IL-1beta caused a slight increase, the difference did not reach statistical significance.

EXAMPLE VIII

Cultured Synoviocytes Express p53 Protein

Figure 3:
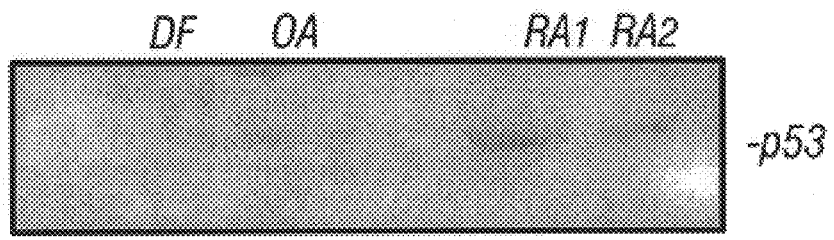
FIG. 3 shows a Western blot experiment demonstrating immunoreactive p53 protein in rheumatoid arthritis fibroblast-like synoviocytes. The demonstration of constitutive p53 expression suggests aberrant p53 regulation.

Because of the putative relationship between apoptosis and expression of p53, we performed preliminary studies to determine if FLS express the p53 protein. Two rheumatoid arthritis and one osteoarthritis FLS lines were cultured to confluency. The lines were approximately matched for passage number. Cells were solubilized and Western blot analysis was performed on the lysate. 40 ug of total cellular protein was loaded into each lane and p53 was detected using monoclonal antibody DO7 (Dako, Carpenteria, Calif.) and a horseradish peroxidase-conjugated secondary antibody. DO7 recognizes both wild type and mutant p53 at amino acids 19–26. FIG. 3 shows that a single p53 band was observed in both rheumatoid arthritis lines, and a less intense band was observed in the osteoarthritis line. A dermal fibroblast line (DF), in contrast, was negative.

Expression of p53 Protein in Cultured Fibroblast-Like Synoviocytes (FLS)

In light of prominent p53 staining in the RA intimal lining, p53 expression was then examined in cultured FLS using flow cytometry. Because p53 is an intracellular antigen, cells were permeabilized with paraformalehyde and saponin to increase antibody penetration. Table 4 shows that nearly 50% of RA FLS constitutively express immunoreactive p53 (n=7). A representative histogram is shown in FIG. 3. Although there was a trend towards greater amounts of p53 protein in RA FLS compared to OA FLS (n=4), the difference did not reach statistical significance.

TABLE 4

Expression of p53 protein in FLS by flow cytometry

|  | % positive | MFC* |
| --- | --- | --- |
| RA (n = 7) | 50.9 ± 7.9 | 35.9 ± 7.7 |
| OA (n = 4) | 44.2 ± 2.9 | 24.4 ± 6.3 |

*MFC = mean fluorescence channel

Confirmation of the constitutive p53 expression by RA FLS, was achieved by western blot analysis also performed on FLS lysates. The Western blots demonstrated that RA FLS expressed significantly more p53 than either OA FLS or dermal fibroblasts (DF). All RA lines studied with this technique (n=11) showed abundant immunoreactive p53. The intensities of the bands were similar over various passage numbers (i.e., from 2–8). In OA FLS (n=4; passages 2–8), p53 was also detected, although the amount was substantially less than in RA. Cultured DF contained only very small amounts of p53, alhtouhd it could be induced to the level of RA FLS upon exposure to ultraviolet light (UV). Using densitometry, the expression of p53 was 74.2±4.5 absorption units (AU) in RA FLS, 24.0±5.8 AU in OA FLS, and 4.0±2.4 AU in DF (p<0.001 for RA vs. OA and RA vs. DF; p≦0.05 for OA vs. DF).

EXAMPLE IX

The Intracellular Location of P53 Protein

Figure 5:
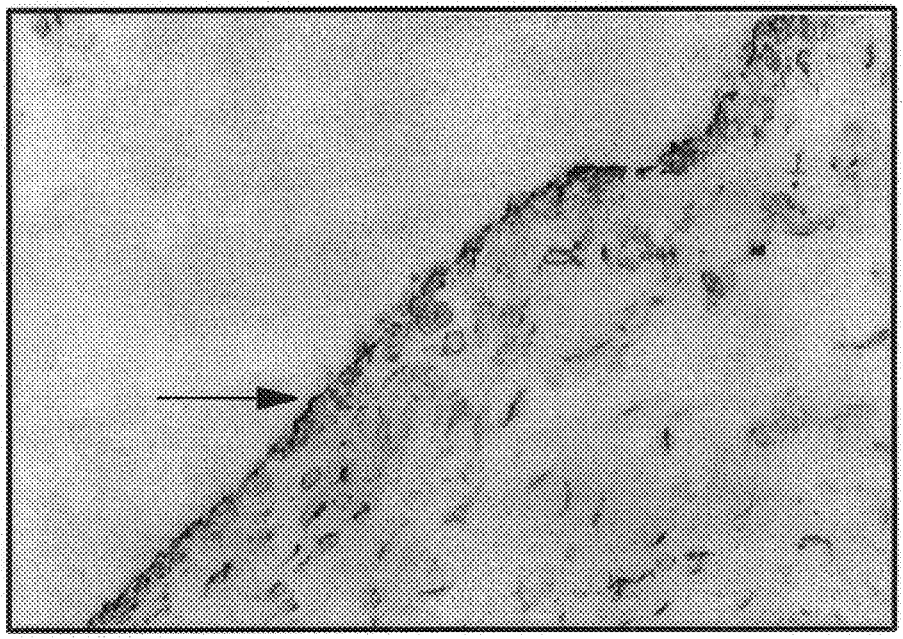
FIG. 5 shows the distribution of mutant p53 protein using a monoclonal antibody that only detects a mutant form of p53 (monoclonal antibody PAb 240 (Oncogene Sciences, Cambridge, Mass.)). Cells in the synovial lining stain with the mutant-specific antibody and immunohistochemistry (see arrow).

The intracellular location of p53 protein is an important determinant of its functional capabilities. It is known that p53 can reside in the cytoplasm (generally bound to hsc70) but is transported to the nucleus after DNA damage or proliferative signals. Our studies of intact tissue showed both cytoplasmic and nuclear staining (see FIG. 1). Immunohistochemistry was then performed on cultured RA FLS to determine the subcellular localization of p53. Our results demonstrate that in FLS cultured in chamber slides, p53 is localized to the cytoplasm of most of these resting cells, with nuclear staining in 10.7±2.4% (see FIG. 5). However, if the cells were exposed to hydrogen peroxide ($H_2O_2$ for 100 min.), nuclear p53 protein expression was markedly increased, while staining in the cytoplasm was diminished. 8–9 hr after stimulating, 70.7112.8% of FLS demonstrated prominent nuclear staining (see FIG. 5) (p=0.003 compared with medium alone; n=3). Dermal fibroblasts behaved similarly, with nuclear staining increasing from 5±1% of cells to 75±17% after exposure $H_2O_2$.

EXAMPLE X

Normal p53 Protein is Present in Rheumatoid Arthritis Synovium

Figure 4:
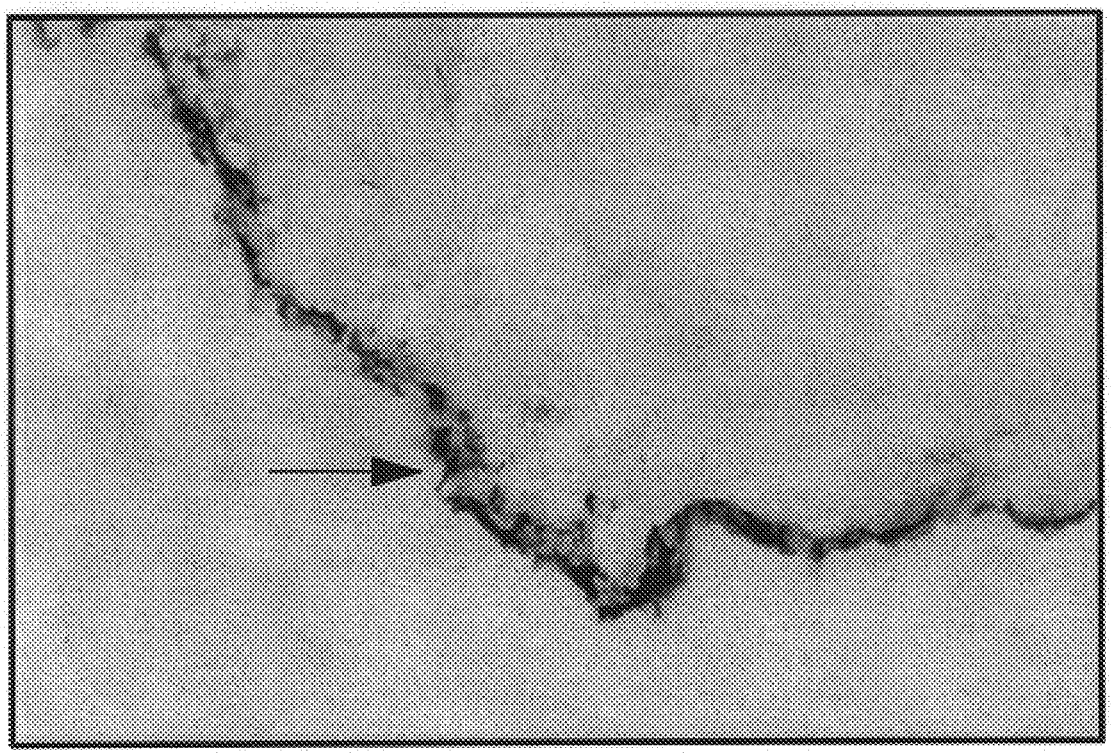
FIG. 4 shows the distribution of p53 in rheumatoid arthritis synovium using an antibody that detects both wild type and mutant p53 protein (D07, Dako, Inc., Carpenteria, Calif.) and immunohistochemistry. The protein is strongly expressed in the intimal lining.

The observations that FLS express p53 protein and that synovial lining cells have DNA fragmentation consistent with apoptosis prompted us to look for p53 protein expression in rheumatoid arthritis synovium. Immunoperoxidase studies on frozen sections of rheumatoid arthritis synovium using an antibody that detects wild type and mutant p53 (DO7) showed that p53 protein was present and expressed mainly in the synovial intimal lining (see arrow on FIG. 4).

EXAMPLE XI

Mutant p53 Protein is Present in Rheumatoid Arthritis Synovium

Using the immunoperoxidase technique and a monoclonal antibody that detects a mutant form of p53 but not wild type (PAb240, which binds to amino acids 212–217), staining was also observed in rheumatoid arthritis synovial tissue. The distribution was similar to that of the pan-p53 antibody, i.e., primarily the synovial intimal lining with lesser amounts of sublining staining (see arrow). Therefore, an immunoreactive form of mutant p53 is present in rheumatoid arthritis synovium in both macrophages and fibroblast-like cells.

EXAMPLE XII

The Presence of Mutant P53 mRNA in Rheumatoid Arthritis Synovium is Confirmed by PCR A sample of cDNA was prepared from rheumatoid synovium that had been obtained at the time of joint replacement surgery. The p53 DNA was amplified by the polymerase chain reaction and cloned into an expression vector. Anti-sense RNA was transcribed from the insert, hybridized to wild type p53 DNA, digested with RNASE A to detect mismatched nucleotides. The fragments were resolved by agarose gel electrophoresis. Ethidium staining revealed evidence of both the wild type p53 as well as shorter fragments due to mutant p53 RNA. This confirms the immunohistochemistry studies and proves that mutant p53 exists in rheumatoid arthritis synovium.

EXAMPLE XIII

Detection of Mutant p53 in Specimens from Patients

The somatic mutations in p53 that occur in the joints of patients with severe chronic rheumatoid arthritis were further analyzed and sequenced. Although analysis of genomic DNA was used for the initial screenings, there were some difficulties due to the occurrence of polymorphisms in the introns, and therefore cDNA derived from the joint tissue was utilized as a first step towards identification of possible mutations.

Table 5 shows the results with 8 RA patients and one control sample. Several of the DNA samples revealed mismatches in p53 cDNA prepared from RA synovium, and in two cases the same mismatches were not found in skin from the same individual. In order to identify the mutation responsible, it was necessary to subclone the amplified region and sequence subclones carrying the mismatch (this is outlined in more detail below). The results below show that three mutations have been identified from two patients, including one silent mutation, one frame shift, and one missense. The latter two were identified in different subclones from the same patient. The frameshift mutation occurs in Exon 11, a region responsible for nonspecific DNA binding, and this results in extensive substitution throughout the end of the molecule (with termination occurring near the wild type site). The missense mutation is more intriguing as it results in an Asn>Ser substitution at residue 239, a substitution that is common in human cancers (Hollstein, et al., *Nucl. Acids Res.*, 22: 355 1, 1994).

TABLE 5

Mutations in p53 in Patient Specimens

| PATIENT | TISSUE | EXONS | MISMATCH | MUTATIONS |
|---|---|---|---|---|
| RA#1 | synovium | 6–10 | yes | |
| RA424 | synovium | 6–10 | yes | Exon 7 mismatch in genomic DNA |
| RA429 | synovium | 6–10 | yes | 3 mutations found in different clones; N239S, R333H, FS370→. Exon 7 mismatch in genomic DNA. |
| RA430 | synovium | 6–10 | yes | 2 mutations found in different clones; V203V, I232M |
| RA431 | synovium | 6–10 | yes | |
| RA433 | synovium | 6–10 | yes | Mismatch found in synovium, not skin |
| | skin | 6–10 | no | |
| RA435 | synovium | 4–10 | yes | Silent mutation in Ex6; |
| | skin | 6–10 | no | L188L. Not found in skin. |
| RA437 | synovium | 6–10 | no | |
| RA446 | synovium | 6–10 | yes | FS225→ |
| normal | blood | 6–10 | no | n = 5; control |
| OA | synovial genomic DNA | 6–7 | no | n = 5; control |
| OA | synovium | 6–10 | no | n = 4; control |
| OA | skin | 6–10 | no | n = 6; control |
| OA | blood | 6–10 | no | n = 4; control |

Possible mutations in p53 identified by mismatch detection using cDNA derived from the indicated tissue as a template. RA indicates that tissue is from a patient with severe rheumatoid arthritis. FS = frame shift. Other mutations indicated by amino acid change and position (e.g., R333H = arginine to histadine at amino acid 333).

As a first step towards proving that this substitution arose as a bona fide somatic mutation in the joint, Exon 7 (where residue 239 resides) was amplified from genomic DNA prepared at the same time as the cDNA from this joint and analyzed this for mismatch as described in the above examples (FIG. 1). Strikingly, a mismatch was observed in this exon, as predicted from the cDNA analysis. An exon 7 mismatch was observed in another sample (where we had seen this before), but not in controls or samples from another patient. Cloning of the amplified product and sequencing of the clones containing a mismatch show whether it is the same mutation observed in the cDNA. If so, blood and/or skin from this patient is isolated to confirm that the mutation is unique to the joint, and thus somatic. As it currently stands, these results (as well as the frame shift mutation we observed in Exon 11) represent strong evidence that p53 mutations exist in RA joints.

As mentioned above, the approach to identifying and characterizing somatic mutations in p53 in tissue samples (FIG. 1) has been modified. Since it is expected that at best only a subset of cells will have mutant p53, simply sequencing DNA or (cDNA) from RA synovium will not identify mutants. Therefore, it is necessary to identify clones that carry mismatches and sequence these to characterize the mutations. Since analysis has been confounded by intron polymorphisms, initial screens were performed using cDNA. The cDNA was amplified using Pfu polymerase which has a higher fidelity than Taq and transcripts generated from the product. If a mismatch is detected, the PCR product is then cloned and subclones are similarly checked for presence of the mismatch.

As expected, the mismatches have been found to be present in less than 30% of the subclones examined (range 10–30% for a small number of samples). These are then sequenced to identify the mismatch. Based on this, genomic DNA which is amplified in the region of the detected mutation is examined and assessed for mismatch. If detected, subclones are checked and sequenced to independently confirm that the mutation is present in the genome. At the same time, cDNA and/or genomic DNA from the same patient but from other tissues (skin, blood) is examined to determine whether the detected mismatches are indeed somatic mutations presently only in the joint. This approach constitutes a strong demonstration of somatic mutation in p53 in chronic RA joints.

EXAMPLE XIV

Occurrence of Apoptosis in Inflammation

The above examples demonstrate that DNA fragmentation and apoptosis occur in the synovium of patients with rheumatoid arthritis. To show that programmed cell death is a generalized phenomenon of inflammation, a mouse air pouch model was established. In this standard model, mice were lightly anesthetized with halothane and 3 ml of sterile filtered air was injected subcutaneously into the back, forming a pocket. This procedure was repeated twice over the next 5 days to form a mature pouch. Subsequently, 3 ml of 1% carrageenan was injected into the pouches. Carrageenan is a highly inflammatory natural substance that, when injected into body cavities, induces leukocyte recruitment, cytokine gene expression, and release of a variety of small molecule mediators. Two days after carrageenan injection, the mice were sacrificed and the pouches were removed. The excised pouches were fixed in formaldehyde and histologic sections were prepared. The sections were subsequently stained using the TUNEL technique (Wood, et al., *Neuron*, 11: 621, 1993) to identify cells with fragmented DNA that were undergoing apoptosis.

In control animal that had been injected with vehicle alone, there was no inflammatory infiltration of the air pouch and very few cells were TUNEL-positive. However, in the carrageenan-injected animals, an inflammatory exudate was present and large foci of TUNEL-positive cells were present in the air pouch tissue. Some of these cells were neutrophils, where apoptosis would be expected. Surprisingly, many mononuclear cells were also TUNEL-positive, indicating that the inflammatory response induced apoptosis in the non-neutrophil population. These studies demonstrate that apoptosis and DNA fragmentation in mononuclear cells (which include macrophages, lymphycytes, and/or fibroblasts) are not specific to rheumatoid arthritis but can occur in a variety of inflammatory settings. Moreover, defective apoptosis will lead to an over-accumulation of cells and exacerbate the inflammatory process. Techniques to correct an apoptosis defect will limit the cellular accumulation and suppress the inflammatory response.

Other Embodiments

In other embodiments, the invention includes the prevention of macrophage accumulation by gene therapy or direct application any protein which is substantially identical in biological activity to a mammalian p53 polypeptide; such homologs include other substantially pure naturally-occurring mammalian p53 proteins as well as allelic variants; natural mutants; induced mutants; DNA sequences which encode proteins and also hybridize to the p53 DNA sequences under high stringency conditions or, less preferably, under low stringency conditions (e.g., washing at 2×SSC at 40° C. with a probe length of at least 40 nucleotides); and proteins specifically bound by antisera directed to a p53 polypeptide so long as such polypeptides have p53 biological activity. The invention also includes use of chimeric polypeptides that include a portion of the 53kD p53 polypeptide.

The invention further includes use of analogs of any naturally-occurring p53 polypeptide which have p53 biological activity. Analogs can differ from the naturally-occurring p53 protein by amino acid sequence differences, by post-translational modifications, or by both. Analogs of the invention will generally exhibit at least 85%, more preferably 90%, and most preferably 95% or even 99% identity with all or part of a naturally-occurring p53 amino acid sequence. The length of sequence comparison is at least 15 amino acid residues, preferably at least 25 amino acid residues, and more preferably more than 35 amino acid residues. Modifications include in vivo and in vitro chemical derivations of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring p53 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual*; current edition, or Ausubel et al., supra). Also included are cyclized peptides, molecules, and analogs which contain residues other than L-amino acids, e.g., D-amino acids or non-naturally occurring or synthetic amino acids, e.g., β or α amino acids.

In addition to full-length polypeptides, the invention also includes p53 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids of the 5 kD protein. Fragments of p53 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

All publications and patent applications mentioned in this specification are herein incorporated by reference to the same extent as if each independent publication or patent application was specifically and individually indicated to be incorporated by reference.

Although the invention has been described with reference to the presently preferred embodiment, it should be understood that various modifications can be made without departing from the spirit of the invention. Accordingly, the invention is limited only by the following claims.

What is claimed is:

1. A method of ameliorating arthritis in a mammal, wherein said arthritis has an etiology associated with a defective apoptosis-regulating gene or polypeptide, the method comprising directly administering to a joint a viral vector comprising a nucleic acid sequence encoding a polypeptide that regulates apoptosis operably linked to a promoter, wherein expression of said nucleic acid sequence results in a modulation of apoptosis such that the mammal exhibits a decreased swelling of joints and/or a decrease in bone loss.

2. The method of claim 1, wherein the modulation is enhancing apoptosis.

3. The method of claim 2, wherein the apoptosis enhancing effect is on fibroblast-like synovial cells.

4. The method of claim 1, wherein the arthritis is rheumatoid arthritis.

5. The method of claim 1, wherein the nucleic acid encodes p53 or FasL.

6. The method of claim 1, wherein the viral vector is a DNA vector.

7. The method of claim 6 wherein the DNA vector is an adenovirus vector.

8. A method for ablating apoptotic defective cells in an arthritic joint comprising:

directly administering to a joint of a mammal an adenoviral vector comprising the DNA sequence encoding p53 operably linked to a promoter, wherein the adenovirus further comprises a deletion of the E1b55K coding region, wherein expression of said DNA sequence results in the ablation of apoptotic deficient cells such that joint swelling and/or bone loss decreases in the mammal.

* * * * *